(12) United States Patent
Hill

(10) Patent No.: US 12,201,973 B2
(45) Date of Patent: Jan. 21, 2025

(54) PIPETTE TIP AND USES AND METHODS THEREOF

(71) Applicant: enicor GmbH, Munich (DE)

(72) Inventor: James Lynn Hill, Feldafing (DE)

(73) Assignee: enicor GmbH, Munich (DE)

( * ) Notice: Subject to any disclaimer, the term of this patent is extended or adjusted under 35 U.S.C. 154(b) by 0 days.

(21) Appl. No.: 18/059,460

(22) Filed: Nov. 29, 2022

(65) Prior Publication Data

US 2023/0158485 A1    May 25, 2023

Related U.S. Application Data

(63) Continuation of application No. 16/093,802, filed as application No. PCT/EP2016/000623 on Apr. 15, 2016, now Pat. No. 11,554,368.

(51) Int. Cl.

| G01N 33/86 | (2006.01) |
| B01L 3/02 | (2006.01) |
| G01N 11/00 | (2006.01) |
| G01N 33/49 | (2006.01) |
| C12N 9/64 | (2006.01) |
| G01N 35/10 | (2006.01) |

(52) U.S. Cl.
CPC ............ *B01L 3/0275* (2013.01); *G01N 11/00* (2013.01); *G01N 33/4905* (2013.01); *G01N 33/86* (2013.01); *B01L 2200/16* (2013.01); *B01L 2300/069* (2013.01); *C12N 9/647* (2013.01); *G01N 2035/106* (2013.01); *G01N 2333/7454* (2013.01)

(58) Field of Classification Search
CPC .... G01N 11/00; G01N 33/4905; G01N 33/86; B01L 3/0275
See application file for complete search history.

(56) References Cited

U.S. PATENT DOCUMENTS

| 5,292,664 A | * | 3/1994 | Fickenscher | ........... | G01N 33/86 |
| | | | | | 436/63 |
| 5,777,215 A | | 7/1998 | Calatzis et al. | | |
| 5,844,686 A | | 12/1998 | Treptow et al. | | |
| 6,343,717 B1 | | 2/2002 | Zhang et al. | | |

(Continued)

FOREIGN PATENT DOCUMENTS

| FR | 2498331 A1 | 7/1982 |
| WO | 2002090995 A2 | 11/2002 |

OTHER PUBLICATIONS

International Search Report and Written Opinion for International Application No. PCT/EP2016/000623 mailed Dec. 12, 2016 (10 pages).

(Continued)

*Primary Examiner* — Brian R Gordon
*Assistant Examiner* — Dwan A Gerido
(74) *Attorney, Agent, or Firm* — Nutter McClennen & Fish LLP

(57) ABSTRACT

The present invention provides a pipette tip, which can be used in in-vitro diagnostics, in particular in the diagnostic testing of body fluids, such as in coagulation testing. The Pipette tip contains two constituents in a spatially separated manner. The present invention furthermore provides a method of performing such diagnostics, e.g. coagulation analysis, and to the use of the pipette tip in such diagnostic testing.

17 Claims, 4 Drawing Sheets

(56) References Cited

U.S. PATENT DOCUMENTS

| | | | |
|---|---|---|---|
| 6,416,716 B1* | 7/2002 | Shukla | G01N 30/6065 |
| | | | 436/174 |
| 6,537,819 B2 | 3/2003 | Cohen et al. | |
| 11,554,368 B2* | 1/2023 | Hill | G01N 11/00 |
| 2002/0081747 A1 | 6/2002 | Jacobs et al. | |
| 2003/0039589 A1 | 2/2003 | Smith | |
| 2003/0153084 A1 | 8/2003 | Zheng et al. | |
| 2004/0071604 A1 | 4/2004 | Kolde et al. | |
| 2005/0045543 A1 | 3/2005 | Gjerde et al. | |
| 2006/0275176 A1 | 12/2006 | Horn et al. | |
| 2010/0081209 A1 | 4/2010 | Brewer | |
| 2010/0167412 A1 | 7/2010 | Xiao et al. | |
| 2010/0190193 A1* | 7/2010 | Calatzis | G01N 33/86 |
| | | | 435/288.1 |
| 2012/0009095 A1 | 1/2012 | Burke et al. | |
| 2013/0102015 A1 | 4/2013 | Schubert | |
| 2016/0320415 A1* | 11/2016 | Manneh | B05D 1/02 |
| 2019/0076838 A1 | 3/2019 | Hill | |

OTHER PUBLICATIONS

International Preliminary Report on Patentability for International Application No. PCT/EP2016/000623 issued Oct. 16, 2018 (7 pages).

\* cited by examiner

PIPETTE TIP AND USES AND METHODS THEREOF

The present application is a continuation of U.S. patent application Ser. No. 16/093,802, filed Oct. 15, 2018; which is a National Stage Entry of PCT/EP2016/000623, filed Apr. 15, 2016; the full disclosures of which are incorporated by reference herein in their entirety.

The present invention relates to the field of in-vitro diagnostics, in particular to the diagnostic testing of body fluids, such as blood samples. More specifically, the present invention relates to a pipette tip, which can be used in in-vitro diagnostics, in particular in the diagnostic testing of body fluids, such as in coagulation testing. The present invention also relates to a method of performing such diagnostics, e.g. coagulation analysis, and to the use of the pipette tip in such diagnostic testing. For many of these diagnostic methods, the body fluid has to be mixed with other reagents to enable, or at least to improve, the diagnostic detection of certain parameters to be measured. For example, in coagulation testing the patient's blood sample has to be combined with special "activator" reagents to simulate clotting processes. In hemorheologic coagulation tests (also called "viscoelastic analysis"), the blood sample is mixed additionally with further coagulation modifiers, such as platelet inhibitors, heparin inhibitors and/or lysis inhibitors.

The coagulation of blood is a highly complex process, starting with liquid blood and ending with the formation of a solid clot. It is an important part of hemostasis, i.e. the cessation of blood loss from a damaged vessel, wherein a damaged blood vessel wall is covered by a blood clot to stop hemorrhage and aid repair of the damaged vessel. Disorders in the coagulation balance can lead to increased hemorrhage and/or thrombosis and embolism.

In a normal individual, coagulation is initiated within about 20 seconds after an injury occurs to the blood vessel damaging the endothelial cells. Platelets immediately form a hemostatic plug at the site of injury. This process is called primary hemostasis. Secondary hemostasis follows if plasma components called coagulation factors respond in a complex cascade to finally form fibrin strands to strengthen the platelet plug.

The coagulation cascade of secondary hemostasis has two pathways, the Contact Activation pathway (formerly known as the Intrinsic Pathway) and the Tissue Factor pathway (formerly known as the Extrinsic pathway) that lead to fibrin formation. It was previously thought that the coagulation cascade consisted of two pathways of equal importance joined to a common pathway. It is now known that the primary pathway for the initiation of blood coagulation is the Tissue Factor pathway. The pathways are a series of reactions, in which a zymogen of a serine protease and its glycoprotein co-factor are activated to become active components, which are then able to catalyze the next reaction in the cascade. Coagulation factors are generally indicated by Roman numerals from I-XIII, with a lowercase 'a' appended to indicate the activated form. Thereby, a fibrin clot is formed, which strengthens the platelet plug.

However, to avoid thrombosis and embolism, the formation of fibrin clots is tightly controlled. The fibrin clot, i.e. the product of coagulation, is broken down in a process called fibrinolysis. Accordingly, fibrinolysis prevents blood clots from growing and becoming problematic. In fibrinolysis, the enzyme plasmin plays a major role, since plasmin cuts the fibrin mesh at various places, leading to the production of circulating fragments that are cleared by other proteases and/or by the kidney and/or liver. Plasminogen is converted to active plasmin by tissue plasminogen activator (tPA) and urokinase, thereby allowing fibrinolysis to occur.

The detection of normal or decreased functionality of these coagulation and/or fibrinolysis components is important in order to assess patients' hemostasis disorders. If a hemostasis disorder is identified, a selected therapy can be applied for example to stop a bleeding.

Several methods of measuring the coagulation characteristics of blood are known. Some such devices attempt to simulate the natural flow of blood in the veins and arteries of a living subject, while other measurement techniques are performed in static blood volumes.

An accurate measurement of the ability of a patient's blood to coagulate in a timely and effective fashion is crucial to certain surgical and medical procedures. Rapid and accurate detection of abnormal coagulations is also of particular importance with respect to appropriate treatment to be given to patients suffering from clotting disorders. Often the condition of such patients makes it necessary to administer blood components, anti-coagulants, certain fibrinolytic agents, anti-platelet agents, or compounds inducing the reverse effects of said agents. In these cases, the treatment dose can be adapted to the extent of a clotting disorder previously determined.

Measurements of blood clotting are provided by various devices, for example as disclosed in U.S. Pat. No. 5,777,215 A and in U.S. Pat. No. 6,537,819 B2. These devices measure the mechanical properties of the clot throughout its structural development. These systems are summarized under the term "viscoelastic methods", as they continuously detect viscoelastic properties of the blood clot while its formation and lysis. Viscoelastic measurements of clotting blood are commonly also referred to as thromboelastography (TEG) measurements.

A number of references describe instruments for measuring blood clotting characteristics based upon mechanical movements. These instruments monitor the elastic properties of blood as it is induced to clot under a low shear environment, i.e. in static blood volumes. The patterns of change in shear elasticity enable the determination of the kinetics of clot formation, as well as the strength and stability of the formed clot. The strength and stability of the clot provide information about the ability of the clot to perform the "work of hemostasis" (i.e., stop or prevent abnormal bleeding) and about the adequacy of blood platelet-fibrin interaction. The kinetics of clot formation mainly provides information about the functionality of coagulation factors. Analysis of all of this information provides results which are useful to predict bleeding, to monitor and manage thrombosis, or to monitor fibrinolysis.

Moreover, as the clotting process consists of various interlinked components, specific activators and inhibitors of the clotting process may be applied in order to detect hemostasis disorders more specifically. Such reagents useful in viscoelastic analysis may comprise an initial activator (e.g., an activator of either the intrinsic or the extrinsic pathway), one or more inhibitors (e.g., fibrinolysis inhibitors, heparin inhibitors, platelet inhibitors), one or more further specific factor(s) of the coagulation cascade, calcium ($CaCl_2$)), phospholipids, and/or stabilizers.

Different reagent concepts for modified viscoelastic measurements are described in the literature, including (i) Reo-Pro-modified TEG as described in Wenker et al.: Thromboelastography, The Internet Journal of Anesthesiology, 2000, Volume 1 Number 3, http://www.ispub.com/ostia/index.php?xmlFilePath=journals/ija/vol1n3/teg.xml and Ruttmann et al.: Hemodilution Enhanced Coagulation Is Not Due to Platelet Clumping, Anesthesiology 2004; 101: A150; (ii) Recombiplastin- and ReoPro-modified TEG as described in http://www.tranfusionguidelines.org.uk/docs/pdfs/bbt_app-use_teg-sop-example.pdf; and (iii) TF- and Trasylol-modified TEG as described in Tanaka et al.: Evaluation of a novel kallikrein inhibitor on hemostatic activation in vitro, Thrombosis Research, Volume 113, Issue 5, 2004, Pages 333-339, whereby TF- and Trasylol-modified TEG is based on the combination of commercially available activator reagents intended for other tests, such as the prothrombin time activator Innovin or Recombiplastin®, combined with customer-made $CaCl_2$) solution and drugs, such as ReoPro® (abciximab) and Trasylol® (aprotinin).

However, in those described concepts standardization is low and many complicated pipetting steps are included, resulting in many sources of user error.

There are other reagent systems on the market, which are based on a variety of reagents. For example, ROTEM® analysis (Manufacturer: Tem Innovations GmbH, Munich, Germany) provides a reagent system for viscoelastic measurements, which is based on standardized reagents, most of which are provided to the customer in a liquid form, which are pipetted by the user into the test cup using standardized operating procedures. This standardizes the application, however, it still requires several pipetting steps for the analysis. For example, to perform a platelet inhibited test together with an extrinsically activated test, the pipetting of blood, $CaCl_2$) solution, extrinsic activator and a platelet inhibitor may result in the performance of a total of eight pipetting steps (including three times changing of the tip during one test procedure) and the need for three different reagents that have to be handled by the user. This provides a requirement for training, consumes time, and is a potential source of error.

Some of the further reagent systems on the market are liquid, and have to be pipetted into a cup (e.g. $CaCl_2$) solution), some are provided in dried form in the measurement cup (such as heparinase) and some are provided in small vials, in a quantity intended for one test. A characteristic of these reagents is that still each reagent is typically provided singly, and therefore several steps are required at least for tests requiring more than one active reagent.

To provide a simpler reagent system for viscoelastic measurements of blood or blood components, the provision of stable liquid combinations of the reagents in the working concentration was investigated. However, no such stable liquid combination could be achieved due to the mutual interactions of the different substances while being mixed together for a longer period. Some components negatively affect the stability of each other when kept mixed together in the liquid phase at higher concentrations; for example, $CaCl_2$) disturbs the stability of Tissue Factor reagent in liquid phase over the time. Moreover, if these combined reagents are provided in an amount sufficient for exactly one test, another problem arises: the very small portion of a liquid reagent might stick to parts of the reagent container or the cap and might thus not mix sufficiently with the sample, i.e. the test liquid, when the analysis is performed.

To avoid these problems, Kolde et al. disclosed in US 2004/0071604 A1 a system providing freeze-dried reagents separately in their working concentrations for one test in a measurement cup (which receives the volume of the sample during measurement). In particular, Kolde et al. disclose a cup system for viscoelastic analyses, in which the lower end of the cup is divided in several sections or 'reagent chambers'. This allows to place the reagents independently into the different chambers, without mixing them and then to freeze-dry the reagents.

However, disadvantages of this solution include the need for a very precise pipetting process, as the separate reagent chambers are very small (<5 mm diameter). Another problem is that the reagent drops might 'jump' out of their section as induced by vibrations in the reagent filling line and mix with each other. A further problem is possible air-drying of the small reagent drops during the processing under room conditions before the lyophilization process begins.

Calatzis et al. disclosed in US 2010/190193 A1 another option by providing freeze-dried reagents all mixed together in their working concentrations for one test in a measurement cup or in a standard reagent container. Thereby, it is suggested that all reagents are co-lyophilized in one reagent container or directly in the measurement cup.

This approach, however, can induce instabilities and variances in the production process due to mixing of all reagents and resulting mutual interaction during the freezing process. Instabilities can also be induced during the freezing process due to corresponding well-known changes in the pH conditions of the reagent mix. Accordingly, Calatzis et al. suggested to stabilize the production process by diluting the reagent mix well below the concentration that is required in viscoelastic testing and compensate for the lower reagent content by proportionally increasing the lyophilized volume. But since the costly freeze-drying process is disproportionally prolonged by such volume increases, this approach reduces the production efficiency considerably. Moreover, co-lyophilized formulations can be substantially less stable than the separated components depending on the residual moisture in the lyophilized reagent compound, which requires even longer processing time during production.

One further shortcoming of the systems disclosed in US 2004/0071604 A1 and in US 2010/190193 A1 is that protein stabilizers are required that can later interfere with the adhesion strength of the blood clot on the cup surface during the viscoelastic measurement.

To overcome the above-mentioned problems, Schubert et al. disclosed a further option in US 2013/102015 A1, where each reagent is diluted separately in an excipient solution and lyophilized in the form of small pellets made of the excipient framework. This approach keeps the reagents apart during the whole production process as well as during storage and minimizes in this way all mutual interactions. On the other hand, an additional component—the excipient—has to be added and must be extensively verified for eventual interference with the coagulation characteristics. Besides this, the process of pellet production becomes considerably more costly than liquid dispensing. It requires highly individual equipment for both, pellet production and later pellet distribution into reagent containers or measurement cups.

In view of the above, it is the object of the present invention to overcome the drawbacks of current reagent systems for viscoelastic analysis outlined above and to provide a pipette tip, which can be used for diagnostic testing such as viscoelastic analysis, as well as respective methods, which are simplifying diagnostic methods such as viscoelastic analysis, for example by minimizing the number of pipetting steps. Moreover, it is also an object of the present invention to provide a pipette tip, which can be used in viscoelastic analysis, wherein the required reagent composition has an improved long-term stability but does not require costly manufacturing equipment or additional (excipient) materials in the reagent composition. It is also an object of the present invention to provide a pipette tip for viscoelastic analysis, and methods and uses thereof which allow for a safe, reproducible and easy to use procedure for different tests. It is also an object of the present invention to provide a pipette tip, which can be used in viscoelastic analysis, and relating methods, which require only standard filling and drying procedures during production without individually specialized and costly automation equipment, thereby allowing cost-saving production. It is a further object of the present invention to provide a diagnostic method, which provides reliable and reproducible results, is easy to handle and which provides a standardized system for the determination of the coagulation characteristics of a blood sample.

The above objects are achieved by means of the subject-matter set out below and in the appended claims.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

Pipette Tip

In a first aspect the present invention provides a pipette tip comprising a constituent (A) and a constituent (B) in a spatially separated manner, wherein the constituents (A) and (B) are adapted to form a diagnostic composition upon combination.

In other words, the constituents (A) and (B) are adapted to form a diagnostic composition upon combination of the constituents (A) and (B), i.e. the diagnostic composition corresponds in particular to a combination of the constituents (A) and (B). Thus, the components comprised by the diagnostic composition are comprised by one or both of the constituents (A) and (B). Preferably the diagnostic composition comprises at least the following components (i) and (ii):
  i) an activator of coagulation; and
  ii) a calcium salt.

As used herein, a "pipette tip" is the tip of a pipette. A pipette is a laboratory tool commonly used to transport a measured volume of liquid. Pipettes come in several designs for various purposes with differing levels of accuracy and precision, from single piece glass pipettes to more complex adjustable or electronic pipettes. Many pipette types work by creating a partial vacuum above the liquid-holding chamber and selectively releasing this vacuum to draw up and dispense liquid. Measurement accuracy varies greatly depending on the style.

Preferably, the pipette is an air-displacement micropipette, which is a type of adjustable micropipette that measures volumes between about 0.1 µl-1000 µl (1 ml). These pipettes require disposable tips that come in contact with the fluid. The four standard sizes of micropipettes correspond to four different disposable tip colors:
(1) Pipette "P10" for pipetting a volume of 0.5-10 µl, whereby the corresponding tips are usually of white color;
(2) Pipette "P20" for pipetting a volume of 2-20 µl, whereby the corresponding tips are usually of yellow color;
(3) Pipette "P200" for pipetting a volume of 20-200 µl, whereby the corresponding tips are usually of yellow color; and
(4) Pipette "P1000" for pipetting a volume of 200-1000 µl, whereby the corresponding tips are usually of blue color.

Accordingly, the pipette tip according to the present invention is preferably a disposable pipette tip, more preferably a disposable pipette tip for an air-displacement micropipette, even more preferably a disposable pipette tip for an air-displacement micropipette for pipetting a volume of 5-1000 microliter.

It is also preferred that the pipette tip is the tip of any other pipette, for example the tip of a positive displacement pipette, preferably a disposable tip of a positive displacement pipette, which is in particular a microsyringe (plastic), composed of a plunger which directly displaces the liquid; the tip of a volumetric pipette, the tip of a graduated pipette, or any other type of pipette. Thereby, it is preferred that it is a disposable pipette tip.

In general, the pipette tip according to the present invention, which contains constituents (A) and (B) of the diagnostic composition comprises:

an open upper end fitting to the corresponding end of a pipette; and an open lower end.

The "upper" and "lower" part/end of a pipette tip, as used herein, refer to the (ideal) orientation of the pipette tip in practice: Since it is desirable that the liquid to be pipetted is located only in the lowest part of the pipette tip (to avoid contamination of the pipette and to avoid air bubbles impairing the measurement accuracy of the volume to be pipetted), a pipette is preferably held perpendicular (to the earth's surface). Accordingly, the liquid to be pipetted typically enters the pipette tip via its open lower end (during aspirating) and is also released via the pipette tip's open lower end. The open upper end, in contrast, fits to the corresponding (lower) end of a pipette and is used to fix the pipette tip on the pipette.

Preferably, the open upper end of the pipette tip and the open lower end of the pipette tip have a circular shape. It is also preferred that the open lower end of the pipette tip has a smaller diameter than the open upper end.

Preferably, the pipette tip according to the present invention further comprises at least one region of the inner surface of the pipette tip containing one (single) of the constituents (A) and (B), in particular wherein the constituent (A) or (B) is directly deposited on said inner surface of the pipette tip (i.e. without any further layers/substances between the at least one of the constituents (A) and (B) and said inner surface of the pipette tip; and/or at least one insert containing one (single) of the constituents (A) and (B), wherein the insert preferably comprises a homogenously porous structure, preferably of a natural or artificial polymer.

Preferably, the pipette tip according to the present invention comprises one region of the inner surface of the pipette tip as described above containing constituent (A) and one region of the inner surface of the pipette tip as described above containing constituent (B). Preferably, the pipette tip according to the present invention comprises one region of the inner surface of the pipette tip as described above containing constituent (A) and one insert as described above containing constituent (B). Preferably, the pipette tip according to the present invention comprises one insert as described above containing constituent (A) and one region of the inner surface of the pipette tip as described above containing constituent (B). Preferably, the pipette tip according to the present invention comprises one insert as described above containing constituent (A) and one insert as described above containing constituent (B). More preferably, the pipette tip according to the present invention comprises (i) one region of the inner surface of the pipette tip as described above containing constituent (A) and one insert as described above containing constituent (B) or (ii) one insert as described above containing constituent (A) and one region of the inner surface of the pipette tip as described above containing constituent (B). Most preferably, the pipette tip according to the present invention comprises (i) one region of the inner surface of the pipette tip as described above containing constituent (A) and one insert as described above containing constituent (B).

Thereby, constituents (A) and (B) are kept for the (allowed) storage time of the tip.

Common pipetting tips are usually produced by injection molding of transparent polymers like polyethylene, polypropylene, polycarbonate, and many others. Accordingly, the pipette tip is preferably made of plastics, such as polyethylene, polypropylene and/or polycarbonate. Some pipette tips are slightly colored by adding a dye to the raw material and this coloring refers to a certain size of the corresponding pipette (e.g., blue for 1000 µl pipettes and yellow for 100 pipettes). Preferably the pipette tip is molded, more preferably having a coloring (transparent or opaque). Such a color is preferably used to indicate the constituents forming a diagnostic composition upon combination and, thus, to the diagnostic test that can be performed by using this tip.

In the pipette tip, constituents (A) and (B) are present in a spatially separated manner. In other words, in the pipette tip constituents (A) and (B) are not in contact with each other. Such spatial separation thus enables that constituents (A) and (B) are not in contact with each other, thereby avoiding undesired chemical reactions of constituents (A) and (B).

Preferably, the pipette tip comprises
 a) a compartment (a) containing the constituent (A); and/or
 b) a compartment (b) containing the constituent (B).

The term "compartment" as used herein refers to a separate part inside the pipette tip. In other words, constituent (A) is preferably contained in a separate part of the pipette tip and constituent (B) is preferably contained in another separate part of the pipette tip. Preferably, a compartment is structurally confined, e.g. by its structure itself (for example if the compartment is an insert, such as a porous insert), by (side) walls, protrusions, membranes or other confining structures. It is also preferred that a compartment is not (completely) structurally confined, such as distinct compartments in the pipette tip being distinct sections of the pipette tip, such as horizontal (crosswise) sections of the pipette tip or longitudinal sections of the pipette tip—without (constructional) structures for separating one section from another.

Preferably, the compartments (a) and (b) are designed to prevent any contact between constituents (A) and (B), in particular as long as they are in liquid form, e.g. during and/or after the manufacturing/filling process of the tip.

Preferably, the compartments are designed to enable filling with different volumes. In other words, the volumes of the compartments (a) and (b) are preferably different from each other, i.e. the volume of compartment (a) is preferably larger or smaller than the volume of compartment (b). For example, compartment (a) may be filled with less than 5 µl liquid constituent (A) and compartment (b) may be filled with more than 5 µl liquid constituent (B), thereby implying that compartment (a) has a volume of less than 5 µl and compartment (b) has a volume of more than 5 µl. For example, compartment (a) may be filled with less than 2 µl liquid constituent (A) and compartment (b) may be filled with more than 2 µl liquid constituent (B), thereby implying that compartment (a) has a volume of less than 2 µl and compartment (b) has a volume of more than 2 µl. For example, compartment (a) may be filled with less than 10 µl liquid constituent (A) and compartment (b) may be filled with more than 10 µl liquid constituent (B), thereby implying that compartment (a) has a volume of less than 10 µl and compartment (b) has a volume of more than 10 µl. Such volumes enable the preparation of the liquid constituents A and B in their respective optimum concentration, in particular for the intended (blood) sample volume. Accordingly, the different reagent filling volumes might be dependent on the total volume of the pipetting tip. For example, a pipette tip with for a (blood) sample volume of about 300 µl might have one compartment suitable for volumes of more than 5 µl reagent and one compartment suitable for less than 5 µl reagent. For example, a pipette tip with for a (blood) sample volume of about 100 µl might have one compartment suitable for volumes above 2 µl reagent and one compartment suitable for volumes less than 2 µl reagent. For example, a pipette tip for a (blood) sample volume of about 600 µl might have one compartment suitable for volumes above 10 µl reagent and one compartment suitable for volumes less than 10 µl reagent.

Preferably, at least one of compartments (a) and (b) is formed by a (porous) insert. Accordingly, the pipette tip preferably comprises at least one (porous) insert. Preferably, constituent (A) is comprised by (exactly) one (porous) insert and/or constituent (B) is comprised by (exactly) one (porous) insert. If both, constituents (A) and (B) are comprised by (porous) inserts, the (porous) insert comprising constituent (A) is preferably different from the (porous) insert comprising constituent (B) in order to ensure spatial separation of constituents (A) and (B). More preferably, compartment (b) containing constituent (B) is formed by a (porous) insert. The term "insert" as used herein refers to an element, which is not comprised by conventional (non-prefilled/non-modified) disposable pipette tips. Typically, an "insert" is made of a material different from the material of the pipette tip itself. However, the insert may also be made of the same material as the pipette tip. The term "porous" refers to an insert having pores as described below. Preferably, the pores of the porous insert have a minimum pore diameter of 2 µm and a maximum pore diameter of 2.0 mm depending on the inner diameter of the pipette tip in the region where the porous insert is placed as described below.

Preferably, the shape of the pipette tip is adapted to receive an insert, in particular a porous insert (herein also called "plug"), preferably in the lower part of the pipette tip. The (porous) insert has preferably a cylindrical or spherical shape. To receive a (porous) insert, the pipette tip may have a conventional (merely conical) shape or the shape of the tip may be modified. Preferably, the shape of the tip may be modified in comparison to the shape of a regular conical pipette tip in a way that the insert can be made of a cylindrical shape. In particular, it is preferred that such a preferred modified pipette tip has as a barely conical, but nearly cylindrical shape, more preferably a cylindrical shape, over at least 2 mm of its entire length. Such a modified pipette tip can receive a cylindrical plug, and a conical shape of the insert can be avoided. Cylindrical plugs are easier and cheaper to produce than conical inserts because they can be blanked directly from sheet material. It is also preferred that the pipette tip is not modified and has, thus, a conventional (merely conical) shape.

Preferably, the porous insert is made of a support material. A "support material" preferably allows absorption of the (initially) liquid constituent (A) and/or (B), e.g. during the manufacturing/filling process of the pipette tip. The term "support material" as used herein refers to a material "supporting" a constituent comprised by the pipette tip, in particular a material "supporting" constituent (A) or constituent (B) comprised by the pipette tip as described herein. In other words, a constituent, in particular constituent (A) or constituent (B), comprised by the pipette tip as described herein may be deposited on a support material. Accordingly, a support material preferably provides a support structure for a constituent, in particular constituent (A) or constituent (B), comprised by the pipette as described herein. Preferably, the support material is a foam, such as a polymeric foam, e.g. a natural or an artificial foam, such as for example a polyether foam, a polyesther foam, a polystyrol foam, or a polyurethane foam. More preferably, the support material is an open-cell foam (or sponge) structure, and, even more preferably, the foam structure has a low variation in pore sizes because similar pore sizes and high material homogeneity allow for even distribution of the liquid reagent in the foam plug during the filling process. Preferably, the pore size, in particular the minimum diameter of the pores, of the support material is at least 2 µm, thereby (i) allowing all possibly apparent components of a human sample liquid (such as blood thrombocytes or red cells; bacteria in urea, etc.) to pass through the porous insert (made of the support material) during sample aspiration, (ii) allowing the sample to dispense without creating closures in the support material and/or (iii) allowing the sample to dispense without overly reducing its aspiration/dispensing speed (e.g., to more than 15 seconds per full volume of the tip). The maximum diameter of the pores does preferably not exceed values of one third of the inner diameter of the pipette tip in the region, where the porous insert is placed, to enable proper fit and sufficient enhancement of the surface area (e.g., maximum pore diameter of 0.3 mm for a tip having 0.9 mm inner diameter in the region where the porous insert is placed, or maximum pore size of 2.0 mm for a tip having 6.0 mm inner diameter in the region where the support material is placed).

The pore diameter (e.g. a maximum or minimum pore diameter), as used throughout the present description, can be measured by methods well-known to the skilled person, in particular by microscopic imaging. Thereby, microscopy is preferably performed under standard conditions (temperature: 22° C. and absolute pressure: 101.325 kPa), in particular reflecting the pore diameter when the pipette tip is used. Standard computer software for microscopic imaging typically provides tools for measurement taking the resolution into account. Another option for determining the pore diameter, which is, however, less preferred than microscopic imaging, is flow-rate measurement and determination of the pore diameter by using, e.g. Darcy's law.

It is also preferred that the foam-like material has a minimum elasticity modulus of >0.3 N/m$^2$ to enable simple fixation of a predominantly axially symmetrical (e.g., cylindrical or spherical) porous insert, such as a "foam plug", (support material) within the tip by actively pressing it into a region where the inner diameter of the tip is smaller than the outer diameter of the plug and the resulting decompression force keeping the plug in place. Additionally, said minimum elasticity would make the handling of the foam plug during manufacturing easier when compared to materials that react with more inelastic deformation to retention forces, acceleration forces, and other forces that are typical for item handling in automated manufacturing.

The elasticity modulus (e.g. a maximum or minimum elasticity modulus), as used throughout the present description, can be measured by methods well-known to the skilled person, in particular by simple material elongation under tensile stress perpendicular to a defined cross section.

It is further preferred that at least one of compartments (a) and (b) of the pipette tip is formed by a porous insert made of support material, such as a foam plug, having a maximum elasticity modulus of <300 N/m$^2$, which would enable reagent filling by using the suction forces as resulting from compression and subsequent decompression of the foam (sponge principle). The compression forces could be applied directly by the employed filling means, e.g., a dispensing needle, or by additional means.

Of note, the elasticity modulus values described above are to be measured for a macroscopic part of the foam material, in particular as average over a number of polymer walls and enclosed empty spheres (the pores), while the polymer itself might have a considerably larger elasticity modulus when processed differently than with foam extrusion.

In more general, the (porous) insert is preferably made of a plastic material that can be injection-molded, sintered, extruded or foamed with the formation of a rather homogeneous porosity of 2-500 μm pore sizes (minimum pore diameter: 2 μm and maximum pore diameter: 500 μm). Examples of such a plastic material, which is the preferred material of the (porous) insert, include polyethylene, polypropylene, polycarbonate, polyether, polyester, and the like. It is also preferred that the insert is not made of a material containing glass or metal, e.g. sheet metal and/or aluminum foil, more preferably the insert does not contain any glass or metal, e.g. sheet metal and/or aluminum foil. It is also preferred that the pipette tip is not made of a material containing glass or metal, e.g. sheet metal and/or aluminum foil, more preferably the pipette tip does not contain any glass or metal, e.g. sheet metal and/or aluminum foil.

Preferably, at least one of compartments (a) and (b) is formed by a (longitudinal or crosswise) section of the pipette tip comprising a reagent layer. Accordingly, the pipette tip preferably comprises at least one reagent layer. Preferably, constituent (A) is comprised by (exactly) one reagent layer and/or constituent (B) is comprised by (exactly) one reagent layer. If both, constituents (A) and (B) are comprised by reagent layers, the reagent layer comprising constituent (A) is preferably different from the reagent layer comprising constituent (B) in order to ensure spatial separation of constituents (A) and (B) (in other words, the reagent layer comprising constituent (A) has preferably no contact with the reagent layer comprising constituent (B) in the pipette tip). More preferably, compartment (a) containing constituent (A) is formed by a (longitudinal or crosswise) section of the pipette tip comprising a reagent layer. To obtain a reagent layer, the respective constituent (A) or (B) (or its components) is preferably deposited onto the inner surface of the pipette tip. For example, the respective constituent (A) or (B) (or its components) may be deposited onto the inner surface of the pipette tip in its liquid form and thereafter the respective constituent (A) or (B) (or its components) is/are dried, e.g. by lyophilization, heat-drying etc. For example, the respective constituent (A) or (B) (or its components) may be sprayed in micro-drops (preferably drops having a diameter of no more than 100 μm when sprayed onto the inner surface of the tip). Thereby, reagent clustering along the open lower end of the tip (and clogging of that end) is prevented. This furthermore allows wetting of the sidewalls and increases the covered surface, resulting in less reagent layer thickness and corresponding faster dissolution after sample adding.

Preferably, the pipette tip comprises a reagent layer having an even thickness. Preferably, the reagent layer is located at the lowest part of the pipette tip, e.g. within the lowest third of the pipette tip (referring to the pipette tip's volume), preferably within the lowest quarter of the pipette tip (referring to the pipette tip's volume), more within the lowest fifth of the pipette tip (referring to the pipette tip's volume), and most within the lowest sixth of the pipette tip (referring to the pipette tip's volume).

In general, the positions of the at least two compartments (a) and (b) in the pipette tip are variable, but are preferably in the range where the sample liquid (in an amount as required to perform the diagnostic test) can completely wet the corresponding region. Thus, the position of compartments (a) and (b) within the tip is preferably within the lower half of the pipette tip, more preferably within the lowest third of the pipette tip, even more preferably within the lowest quarter (fourth) of the pipette tip, whereby the terms "half", "third" and "quarter (fourth)" refer to the respective volume in relation to the total volume of the pipette tip, i.e. ½ of the total volume, ⅓ of the total volume or ¼ of the total volume.

Preferably, the pipette tip comprises at least one (porous) insert as described herein and at least one reagent layer as described herein. Thereby, it is preferred that the porous insert comprises constituent (A) and the reagent layer comprises constituent (B) or the porous insert comprises constituent (B) and the reagent layer comprises constituent (A). If the pipette tip comprises at least one (porous) insert as described herein and at least one reagent layer as described herein, (i) the at least one (porous) insert as described herein may be located above the at least one reagent layer as described herein (referring to an orientation of the pipette tip as described above, in the context of the "upper and lower part/end" of the pipette tip), or (ii) the at least one (porous) insert as described herein may be located below the at least one reagent layer as described herein (referring to an orientation of the pipette tip as described above, in the context of the "upper and lower part/end" of the pipette tip). Preferably, the at least one (porous) insert as described herein may be located above the at least one reagent layer as described herein (referring to an orientation of the pipette tip as described above, in the context of the "upper and lower part/end" of the pipette tip).

Preferably, at least the compartment having the larger volume as described above is formed by a (porous) insert, e.g. made of a support material. For example, compartment (b) containing the constituent (B) is formed by a (porous) insert, e.g. made of a support material, or compartment (a) containing the constituent (A) is formed by a (porous) insert, e.g. made of a support material.

Preferably, the pipette tip according to the present invention comprises:
  a) a compartment (a) containing constituent (A) and not containing the constituent (B); and
  b) a compartment (b) containing constituent (B) and not containing the constituent (A).

Thereby, it is more preferred that the constituents (A) and (B) are adapted to form a diagnostic composition upon combination, wherein the diagnostic composition (i.e. the constituents (A) and/or (B)) comprises the following components (i) and (ii):
  i) an activator of coagulation; and
  ii) a calcium salt.

Preferably, in the pipette tip according to the present invention as described above, the constituent (A) is different from the constituent (B). In other words, constituents (A) and (B) are preferably not the same.

Since the constituents (A) and (B) are adapted to form a diagnostic composition upon combination, wherein the diagnostic composition preferably comprises the components (i) and (ii), as described above, each of the constituents (A) and (B) is in particular a composition of components (or reagents) by itself. Preferably, constituent (A) is a composition comprising component (i) or component (ii), and, optionally, further components. Accordingly, constituent (B) is preferably a composition comprising component (i) or component (ii), and, optionally, further components. However, constituent (A) is preferably different from constituent (B) and, thus, it is preferred that:
  1) component (i) is comprised by constituent (A) and component (ii) is comprised by constituent (B); or
  2) component (ii) is comprised by constituent (A) and component (i) is comprised by constituent (B).

An exemplary diagram showing a typical coagulation test, namely, a viscoelastic analysis (also referred to as viscoelastic measurement), is shown in FIG. 1. The diagram curve represents the increasing clot firmness in the measurement cup after an initial delay time (clotting time). The curve develops until a maximum is reached that represents the maximum clot firmness of the sample.

By using the pipette tip according to the present invention, a viscoelastic analysis may be performed for example as follows:

1) a defined volume of a sample (e.g., whole blood, blood plasma etc.) is aspirated into a pipette tip containing a constituent (A) of the diagnostic composition in dry, wet, or other formulation and a constituent (B) of the diagnostic composition in dry, wet, or other formulation, thereby obtaining a mixture of constituent (A), constituent (B) and the sample;
2) optionally, a short time delay (e.g., 0-30 s) allowing for complete dissolution of constituents (A) and (B) of the diagnostic composition within the sample liquid;
3) the mixture (or solution) of constituent (A), constituent (B) and the sample is added directly into a measurement cup suitable for viscoelastic measurement;
4) optionally, to improve the mixing of all components, the resulting mixture is at least partially aspirated again into the pipette tip and subsequently released again into the measurement cup (this step may be repeated one or more times); and
5) the viscoelastic measurement is started (after placing the cup in the right measurement position if this has not been done before).

Optionally, the sample may be added to a container containing a further constituent of the diagnostic composition after step 2) and aspired again after a short dissolution time (0-30 s) and before step 3).

Accordingly, the user needs only a minimum of two pipetting steps for each test to perform, while in the liquid reagent system according to the prior art up to eight steps are required. Moreover, no change of the pipette tip is necessary. Thus, the present pipette tip—for example for the determination of coagulation characteristics of a blood sample—can be handled easier, thereby decreasing the likelihood of errors, which can be due to an imprecise line of action by a (potentially less experienced) operator. Therefrom, further advantages may arise as, for example, a higher reproducibility of the results to be achieved, and thus, a higher degree of standardization.

The sample to be tested by use of the pipette tip according to the present invention is preferably liquid. Accordingly, it is also referred to herein to a liquid sample as sample liquid or test liquid. More preferably the sample liquid is a biofluid (also referred to as body fluid), i.e. a fluid originating from an organism, in particular a fluid originating from a human or an animal Even more preferably the sample liquid is blood, preferably whole blood, or one or more of its elements, e.g. plasma and/or cells. Particularly preferably the sample is a human blood sample and comprises (whole) blood and/or blood plasma.

Accordingly, the present invention is directed to a diagnostic composition and a pipette tip, which can be used in in-vitro diagnostics of a sample, such as coagulation tests, in particular in the viscoelastic analysis of a sample. The diagnostic composition preferably contains at least one activator of coagulation and a calcium salt, i.e. components (i) and (ii). Optionally, the diagnostic composition may contain further components as described below, e.g. one or more other inhibitors and/or coagulation components.

According to the present invention, the components of the diagnostic composition are separated within the pipette tip, in particular the components of the diagnostic composition are contained in at least two distinct compartments of the pipette tip. Since a pipette tip and, optionally, a measurement cup are anyway required in in-vitro diagnostics of a sample, such as coagulation tests, in particular in the viscoelastic analysis of a sample, no additional reagent containers are necessary and a loss of diagnostic composition or one or more components thereof, which is due to pipetting from one additional reagent container into another reagent container, can be avoided. Moreover, the present invention allows to provide the required diagnostic composition with improved long-term stability and increased reconstitution time for the contained bio-molecules, but without the need for using costly manufacturing equipment or additional (excipient) materials in the reagent composition. In clinical application of the disclosed pipette tip, the number of pipetting steps is minimized. In particular, the pipette tip according to the present invention is adapted to one single analysis of a blood sample and has a superior reagent stability regarding several prior art compositions. The inventive concept is based on the separation of the required substances, e.g. into two different compartments.

Optionally, the pipette tip according to the present invention may preferably contain one or more further compartments, e.g. 1, 2, 3, 4, or 5 further compartments, in addition to the compartment (A) containing a constituent (A) and compartment (b) containing a constituent (B). Such an additional compartments preferably contain constituents other than constituents (A) and (B), which also contribute to the diagnostic composition formed upon combination of the constituents (A) and (B).

Optionally, one or more additional (reagent) components may be provided by another (reagent) container, such as a regular reagent vial or a measurement cup, in addition to the pipette tip, thereby providing a diagnostic kit.

It is also preferred, however, that the pipetting tip according to the present invention comprises exactly two constituents (A) and (B), i.e. no more constituents in addition to constituents (A) and (B).

Preferably, the pipette tip, which contains constituent (A) and (B) (and any optional additional reagent container) contain in particular a constituent of the diagnostic composition in an amount sufficient for performing one single viscoelastic analysis of a sample, in particular test liquid. In particular, the pipette tip, which contains a constituents (A) and (B) (and any optional additional reagent container) can be filled with reagents in either liquid, dry, essentially dry or any other formulation.

The amount sufficient for performing one single viscoelastic analysis of a sample, for example a blood sample, is that amount required for each of the constituents when all constituents are in mixture (i.e. in the "diagnostic composition"), which provides the required concentration of the reagents in the final diagnostic analysis, e.g. viscoelastic analysis, of the sample, e.g. of a blood sample. Therefore, it is not necessary to further portion the diagnostic composition before or after mixing, preferably dissolving, it in a liquid.

Preferably, the final working concentration of reagents is achieved by mixing, the constituents with the sample directly in the pipette tip, but not by mixing the constituents in an amount of liquid diluent in the pipette tip and bringing this solution together with the intended sample subsequently.

Further, it is preferred that the mixing is achieved by dissolution of the constituents within the sample.

Accordingly, the present invention (1) allows a separation of certain reagent ingredients that influence each other, which increases the reagent stability; (2) allows the formulation of ingredients in either liquid, dry, essentially or other form depending on the their stability and/or stability needs (in particular, some of the ingredients are typically used in huge excess so that partial degradation is not falsifying the test results, some ingredients are typically incredibly stable even in liquid form, and only some ingredients are typically less stable in liquid form and not used in excess and must therefore be treated more carefully); and (3) saves additional costs and material waste (i.e., reagent vials) by employing containers that are used anyway for performing the diagnostic test, such as viscoelastic tests.

Accordingly, the present invention provides a unique combination of two constituents (A) and (B) arranged in a single pipette tip in a spatially separated manner, whereby the pipette tip is used anyway to perform a viscoelastic measurement or other diagnostic measurement. The resulting degree of freedom to formulate the at least two separated parts (i.e. the at least two separated constituents) of the diagnostic composition in either dry, essentially dry, liquid, or any other formulation comprises a new and highly cost-effective approach. The present inventors surprisingly arrived at the present invention based on performing a combination of analyses of the mutual ingredient interactions, performing stability studies in dependence on the formulation as dry, essentially dry or liquid, investigating stability and test performance studies to assess the possible negative impact of the employed containers on the test result in viscoelastic measurements with body liquids like blood or blood plasma (cf. Examples) and, last but not least, understanding the commercial impact on providing a reagent in either excess amount or not.

Preferably, each of the constituents (A) and (B) is independently from each other a liquid formulation, an essentially dry formulation, or a dry formulation.

"Essentially dry" as used herein refers to a state, wherein the mixture is essentially free from any liquid or moisture, in particular being depleted of water. Water or any other liquid, however, may be present as residue in the mixture, but only to an extent, which does not negatively influence the stability of the overall composition. In particular, it has to be excluded that an interaction occurs between the different constituents, which negatively affects the stability. A remaining amount of liquid, preferably water, in the composition of up to 10% by weight may be acceptable in an essentially dry formulation.

More preferably, constituents (A) and (B) are essentially dry formulations or dry formulations, and even more preferably constituents (A) and (B) are dry formulations. For example, it is preferred that either (1) constituent (A) is a dry formulation and constituent (B) is an essentially dry formulation; or (2) constituent (A) is an essentially dry formulation and constituent (B) is a dry formulation. Most preferably, however, both, constituents (A) and (B) are dry formulations.

Thereby, the stability of constituents (A) and (B) under room temperature conditions is enhanced. Nevertheless, constituents (A) and (B) may be filled into the pipette tip, e.g. during the manufacturing process of the pipette tip, in dry, essentially dry or in liquid formulation, for example by employing subsequent vacuum drying, heated drying, lyophilization, or any other process suitable for drying the constituents (A) and (B).

Preferably, in the pipette tip according to the present invention:
1) constituent (A) comprises component (i) but not component (ii) and constituent (B) comprises component (ii) but not component (i); or
2) constituent (A) comprises component (ii) but not component (i) and constituent (B) comprises component (i) but not component (ii).

Thereby, it is understood, that in situation 1), i.e. if component (i) is comprised by constituent (A) and component (ii) is comprised by constituent (B), the constituent (A) does not comprise component (ii) and the constituent (B) does not comprise component (i). Accordingly, in situation 2), i.e. if component (ii) is comprised by constituent (A) and component (i) is comprised by constituent (B), the constituent (A) does not comprise component (i) and the constituent (B) does not comprise component (ii). Thus, each of the constituents (A) and (B) preferably comprises either component (i) or component (ii).

According to the present invention component (i) of the diagnostic composition, i.e. the activator of coagulation, is preferably spatially separated from component (ii) of the diagnostic composition, i.e. the calcium salt. If these components remain spatially separated until shortly before the viscoelastic analysis starts, a superior stability of the diagnostic composition (or the respective components) can be achieved and stability related problems can be avoided. Thus, the constituent (A) of the diagnostic composition preferably comprises either component (i) or component (ii), but not both, component (i) and (ii). Accordingly, the constituent (B) of the diagnostic composition preferably comprises the component selected from component (i) and component (ii), which is not comprised by constituent (A), and also not both, component (i) and (ii).

Although certain embodiments may be preferred, as described below, in general either the activator of coagulation (component (i)) may be contained in constituent (A) and the calcium salt (component (ii)) may be contained in constituent (B) or vice versa.

Diagnostic Composition and Constituents and Components Thereof

In the context of the present invention, the term "diagnostic composition" refers to a reagent composition (reagent mixture) for in-vitro diagnostic analysis, such as coagulation testing, in particular viscoelastic analysis, which is ready-to-use. In other words, in addition to the diagnostic composition and the sample no further reagent is required to perform the diagnostic analysis. Moreover, dilution or the like of the diagnostic composition is not necessary.

In the present invention, the constituents of the diagnostic composition, in particular the constituent (A) and the constituent (B), are spatially separated. As long as the constituents, in particular the constituent (A) and the constituent (B), are spatially separated, they do not yet form a diagnostic composition, however, they are able to form a diagnostic composition. The diagnostic composition is formed by bringing the constituents, e.g. constituent (A) and constituent (B), into contact with each other, preferably by mixing.

The sample may be brought into contact either (i) with the diagnostic composition, i.e. after contacting the constituents of the diagnostic composition with each other, or (ii) with a constituent, e.g. with constituent (A) or constituent (B). In case (ii) the diagnostic composition is formed after contacting the sample with one of the constituents, i.e. the sample is brought into contact with one of the constituents, e.g. with constituent (A), and the other constituent, e.g. constituent (B), is contacted thereafter with a mixture of constituent (A) and the sample, thereby forming a mixture of the diagnostic composition and the sample.

According to the present invention, the pipette tip contains constituents (A) and (B). When the sample is aspirated by the pipette tip the sample either contacts first constituent (A) or constituent (B), or both constituents at about the same time. Even if there are time differences between these two contacts, these temporal differences are rather negligible (typically less than 1 sec) and a mixture of the diagnostic composition and the sample is formed rather instantaneously.

As described above, a diagnostic composition comprises components, which are described in more detail below. Since the constituents of the diagnostic composition are to form the diagnostic composition, the constituents, in particular constituent (A) and constituent (B), comprise the components of the diagnostic composition. Thereby, one or more components of the diagnostic composition may be comprised by constituent (A), one or more components of the diagnostic composition may be comprised by constituent (B), and one or more components of the diagnostic composition may be comprised by both, constituents (A) and (B).

Thus, it is understood, that a component "comprised by the diagnostic composition" is a component, which is comprised by one or both of the constituents, i.e. by the constituents (A) and/or (B). In other words, if the diagnostic composition comprises a certain component, this component is usually comprised by constituent (A) (and not by constituent (B)) or by constituent (B) (and not by constituent (A)) or by both, constituent (A) and (B).

In a preferred embodiment, the diagnostic composition may be for viscoelastic analysis. Thereby, the constituents (A) and/or (B), preferably comprise(s) (i) an activator of coagulation (e.g., an activator of either the intrinsic or the extrinsic pathway), (ii) a calcium salt, and (iii) optionally one or more further inhibitors, e.g. fibrinolysis inhibitors, platelet inhibitors, heparin inhibitors and/or (iv) optionally one or more further specific factors or co-factors of the coagulation cascade.

In another preferred embodiment, the diagnostic composition may be for coagulation diagnostics in blood or blood plasma other than viscoelastic analysis, such as 'Prothrombin Time' (PT), 'Activated Partial Thromboplastin Time' (APTT), 'Activated Clotting Time' (ACT), or 'Prothrombinase Induced Clotting Time' (PICT). Thereby, the constituents A and B are preferably exactly the same as described herein for viscoelastic analysis or the activator may be different. Thus, preferred coagulation activators include FXa and Russel's Viper Venom—Factor V activating component (RVV-V). Moreover, in this embodiment, it may not be necessary to provide a calcium salt in one of the constituents (A) or (B), but to separate other components by dividing them into constituent (A) and constituent (B). For example, in PICT diagnostics the enzyme FXa should be separated from the protein component RVV-V, because the activity of these substances is compromised when they are applied in combination.

Preferably, the activator of coagulation is an extrinsic activator and/or an intrinsic activator, i.e. an activator of the extrinsic pathway (the Tissue Factor pathway) or of the intrinsic pathway (the Contact Activation pathway).

Thereby, it is preferred that:
component (i) is an extrinsic activator of coagulation and component (ii) is a calcium salt; or
component (i) is an intrinsic activator of coagulation and component (ii) is a calcium salt.

The extrinsic activator of coagulation maybe an activator of the Extrinsic Prothrombin Activation Pathway (extrinsic pathway), in particular a Tissue factor (TF, also referred to as platelet tissue factor, factor III, thromboplastin, or CD142). Preferably, the TF is selected from lipidated TF or recombinant TF (rTF).

The intrinsic activator of coagulation maybe any activating factor of the Contact Activation pathway (intrinsic pathway), e.g., celite, ellagic acid, sulfatit, kaolin, silica, or RNA. Preferably, the intrinsic activator of coagulation is selected from celite, ellagic acid, sulfatit, kaolin, silica, RNA, and mixtures thereof.

The pipette tip according to the present invention as described herein may contain a calcium salt, preferably as component (ii). The calcium salt is added for re-calcification of the sample. Blood samples can be prevented from clotting by several different anticoagulatory substances like heparin, EDTA, citrate. Typically functional tests are performed with blood anticoagulated with citrate. Citrate moderately complexes calcium of the blood sample. Calcium is necessary for the coagulation process, it is involved in complex formation and is a co-factor for most of the coagulation factors (e.g., FI, FII, FV, FVII, FVIII, FIX, FX, FXI, FXIII, TF). Therefore, recalcification of the sample is necessary to ensure correct coagulation in the sample, if the sample was for example citrated during blood withdrawal (by using a blood tube containing citrate). Preferably, the calcium salt is calcium chloride and/or calcium lactate and/or calcium gluconate. More preferably, the calcium salt is $CaCl_2$).

Preferably, the calcium salt, in particular $CaCl_2$), is present in an amount of about 1-100 µmol/ml of sample (test liquid), more preferably in an amount of about 3-30 µmol/ml of sample (test liquid). As mentioned above, the amount of the calcium salt, in particular $CaCl_2$, must be sufficient to ensure recalcification of the sample, in particular of the blood sample, if the sample was decalcified before. It turned out that an amount of from 3-30 µmol/ml is particularly optimal to achieve this requirement. In order to determine the required amount of the calcium salt, in particular $CaCl_2$), to be contained in the diagnostic composition, i.e. the constituents (A) and/or (B), even more precisely, the exact volume of the sample to be collected from the patient has to be known as well as the amount of decalcifying reagent employed.

The diagnostic composition, i.e. the constituents (A) and/or (B), may optionally comprise further components. Preferably, the diagnostic composition, i.e. the constituents (A) and/or (B), further comprises one or more components selected from the group consisting of: a further activator of coagulation (i.e. an activator of coagulation as described herein, which is different from the activator of coagulation comprised as component (i); also referred to as "coagulating activating factor"); a coagulation inhibitor (i.e., a substance that stops, reduces, or at least modifies the function of a certain components of the coagulation and/or clot lysis cascade); and an active-component inhibitor (i.e., a substance the stops, reduces, or at least modifies the function of a component active in coagulation, e.g. a coagulation inhibitor). Preferably, the coagulation activating factor is selected from the group consisting of FI, FII, FV, FVII, FVIII, FIX, FX, FXI, FXIII, and TF. Preferably, the coagulation inhibitor is selected from the group consisting of tissue factor pathway inhibitor, antithrombin I-IV, or activated protein C.

Preferably, the active-component inhibitor is selected from the group consisting of one or more platelet inhibitors (i.e., substances that stop, reduce, or at least modify the function of thrombocytes), one or more fibrinolysis inhibitors (i.e., substances that stop, reduce, or at least modify the function of clot lysis), and/or one or more heparin inhibitors. Preferably, the platelet inhibitor is a cytoskeleton inhibitor, preferably Cytochalasin D, or a GPIIb/IIIa antagonist, preferably Abciximab. Preferably, the fibrinolysis inhibitor is selected from the group consisting of aprotinin, tranexamic acid, eaca, thrombin-activated fibrinolysis inhibitor, plasminogen activation inhibitor 1/2, α2-antiplasmin, and α2-macroglobulin. Preferably, the heparin inhibitor is selected from heparinase, protamine or protamine-related peptides and their derivatives, or other cationic polymers, for example hexadimethrine bromide (polybrene). The heparin inhibitor is in particular useful to detect the presence of heparin in the sample and, thus, the amount of heparin inhibitor (e.g., heparinase) is a sufficient to detect the presence of heparin in the sample.

Those inhibitors may be used and combined depending on the precise diagnostic demands, for example, the platelet inhibitor may be a cytoskeleton inhibitor or a GPIIb/IIIa antagonist. The fibrinolysis inhibitor can be selected, for example, from aprotinine, tranexamic acid, or eaca; the heparin inhibitor might be selected, for example, from heparinase, protamine or protamine-related peptides; and the coagulation factor can be selected, for example, from one or more coagulation factors or activated coagulation factors preferably FXa or FVa or activated protein C or FVIIa. However, it is noted that this is only a preferred selection and further inhibitors can be used if required.

Preferably, the diagnostic composition, i.e. the constituents (A) and/or (B), may also contain one or more stabilizers, wherein the stabilizer is preferably albumin or gelatine. Such stabilizers are typically used for the stabilization of the reagents between the time of production and the analysis. Preferably, in the pipette tip according to the present invention, a protein stabilizer, for example albumin or gelatin, is comprised by constituent (A) but is not comprised by constituent (B); or a protein stabilizer, for example albumin or gelatin, is comprised by constituent (B) but is not comprised by constituent (A).

Alternatively, it is also preferred that the diagnostic composition, i.e. the constituents (A) and/or (B), do(es) not contain albumin, more preferably the diagnostic composition, i.e. the constituents (A) and/or (B), do(es) not contain albumin or gelatin, and even more preferably the diagnostic composition, i.e. the constituents (A) and/or (B), do(es) not contain any stabilizer. Most preferably, the pipette tip, and in particular the constituents (A) and (B), do not contain protein stabilizers like albumin. Such stabilizers may interfere with viscoelastic measurements.

Preferably, the diagnostic composition, i.e. the constituents (A) and/or (B), may also contain one or more phospholipids. Phospholipids may be added since several complexes in the coagulation cascade are phospholipid-dependent. Preferably, the phospholipids may be a composition of different phospholipids like for example phosphatidylserine, phosphatidylethanolamine and phosphatidylethanolcholine. Preferably, mixtures of different phospholipids as extracted from biological samples (e.g., rabbit brain) may be used.

Preferably, the phospholipid and/or the heparin inhibitor, preferably heparinase and/or hexadimethrine bromide (polybrene), more preferably hexadimethrine bromide (polybrene), are comprised by constituent (A) and arranged in compartment (a).

Depending on the diagnostic aim, the above described components can be used either alone or in combination: For example, a measurement with only an intrinsic activator in the sample can be combined with a measurement with an intrinsic activator and a sufficient amount of heparin inhibitor (e.g., heparinase) in the sample to detect the presence of heparin in the test liquid; a combination of extrinsic activator and platelet inhibitor (e.g., Cytochalasin D) in the sample can be applied to determine the activity of fibrinogen without platelet contribution in the sample.

Preferably, the diagnostic composition, i.e. the constituents (A) and/or (B), comprise or consist of a combinations of components selected from the following combinations of components:

extrinsic activation: Combination of extrinsic activator and $CaCl_2$) and, optionally, stabilizer(s);

intrinsic activation: Combination of intrinsic activator and $CaCl_2$) and, optionally, stabilizer(s);

extrinsic activation insensitive for heparin: Combination of extrinsic activator, heparin inhibitor, $CaCl_2$ and, optionally, stabilizer(s);

intrinsic activation insensitive for heparin: Combination of intrinsic activator, heparin inhibitor, $CaCl_2$) and, optionally, stabilizer(s);

extrinsic activation without platelet activation: Combination of extrinsic activator, platelet inhibitor and $CaCl_2$) and, optionally, stabilizer(s);

extrinsic activation without platelet activation, insensitive for heparin: Combination of extrinsic activator, platelet inhibitor, heparin inhibitor, $CaCl_2$) and, optionally, stabilizer(s);

extrinsic activation without platelet activation, insensitive for heparin: Combination of extrinsic activator, platelet inhibitor, heparin inhibitor, $CaCl_2$) and, optionally, stabilizer(s);

intrinsic activation without platelet activation: Combination of intrinsic activator, platelet inhibitor, $CaCl_2$) and, optionally, stabilizer(s);

intrinsic activation without platelet activation, insensitive for heparin: Combination of intrinsic activator, platelet inhibitor, heparin inhibitor, $CaCl_2$) and, optionally, stabilizer(s);

extrinsic activation with inhibition of fibrinolysis: Combination of extrinsic activator, fibrinolysis inhibitor and $CaCl_2$) and, optionally, stabilizer(s);

extrinsic activation with inhibition of fibrinolysis, insensitive for heparin: Combination of extrinsic activator, fibrinolysis inhibitor, heparin inhibitor, $CaCl_2$) and, optionally, stabilizer(s);

intrinsic activation with inhibition of fibrinolysis: Combination of intrinsic activator, fibrinolysis inhibitor and $CaCl_2$) and, optionally, stabilizer(s);

intrinsic activation with inhibition of fibrinolysis, insensitive for heparin: Combination of intrinsic activator, fibrinolysis inhibitor, heparin inhibitor, $CaCl_2$) and, optionally, stabilizer(s);

extrinsic activation with additional coagulation factor: Combination of extrinsic activator, one additional coagulation factor and $CaCl_2$) and, optionally, stabilizer(s);

extrinsic activation with additional coagulation factor, insensitive for heparin: Combination of extrinsic activator, one additional coagulation factor, heparin inhibitor, $CaCl_2$) and, optionally, stabilizer(s);

intrinsic activation with additional coagulation factor: Combination of intrinsic activator, one additional coagulation factor and $CaCl_2$) and, optionally, stabilizer(s);

intrinsic activation with additional coagulation factor, insensitive for heparin: Combination of intrinsic activator, one additional coagulation factor, heparin inhibitor, CaCl$_2$) and, optionally, stabilizer(s).

In a first preferred embodiment, constituent (A) comprises at least an extrinsic activator of coagulation, which is preferably selected from TissueFactor (TF), lipidated TF or recombinant TF or any mixtures thereof in dry, essentially dry, or liquid formulation or in any other formulation that allows for dissolution of the TF within 30 s after aspiration of the sample liquid. In the same preferred embodiment, constituent (B) comprises a calcium salt. Preferably, constituents (A) and (B) do not comprise a platelet inhibitor and/or a fibrinolysis inhibitor. This embodiment is referred to as 'EX-tip' in the following and could be used to perform a viscoelastic measurement of the extrinsically activated coagulation pathway.

In a second preferred embodiment, constituent (A) and constituent (B) comprise the components as described for the first preferred embodiment. In addition, either constituent (A) or constituent (B) as described for the first preferred embodiment contains additionally one or more platelet inhibitors, preferably selected from GPIIb/IIIa antagonists, preferably Abciximab, and/or cytoskeleton inhibitors, preferably Cytochalasin D, in dry, essentially dry, or liquid formulation, or in any other formulation that allows for dissolution of the reagent composition within 30 s after aspiration of the sample liquid. This embodiment is referred to as 'FIB-tip' in the following.

In a third preferred embodiment, constituent (A) and constituent (B) comprise the components as described for the first preferred embodiment. In addition, either constituent (A) or constituent (B) from the first preferred embodiment contains additionally one or more fibrinolysis inhibitors, preferably aprotinine, tranexamic acid or eaca, in dry, essentially dry, or liquid formulation, or in any other formulation that allows for dissolution of the reagent composition within 30 s after aspiration of the sample liquid. This embodiment is referred to as 'AP-tip' in the following.

It is also preferred that constituent (A) or (B) according to the three previously described preferred embodiments 'EX-tip', 'FIB-tip' and 'AP-tip' contains in addition one or more heparin inhibitors, preferably protamine or protamine derivatives, whereby preferred protamine derivatives include protamine sulfate and protamine hydrochloride, or other protamine-like peptides and their derivatives, or other cationic polymers, preferably hexadimethrine bromide (polybrene), that have the potential to neutralize the anti-coagulating effect(s) of heparine or heparine-like substances in a blood sample by charge interaction. The resulting reagent composition is preferably a dry, essentially dry or a liquid formulation, or any other formulation that allows for dissolution of the reagent composition within 30 s after aspiration of the sample liquid. Corresponding tips are referred to as 'EX-tip HI', 'FIB-tip HI', and 'AP-tip HI' in the following.

In a fourth preferred embodiment, constituent (B) comprises at least an intrinsic activator of coagulation, which is preferably selected from celite, ellagic acid, sulfatit, kaolin, silica, RNA, or any mixtures thereof in dry, essentially dry, or liquid formulation, or in any other formulation that allows for dissolution of the activator within 30 s after aspiration of the sample liquid. In this embodiment, the constituent (A) comprises a calcium salt and the embodiment is referred to as 'IN-tip' in the following.

In a fifth preferred embodiment, constituent (A) and constituent (B) comprise the components as described for the fourth preferred embodiment. In addition, either constituent (A) or (B) of the 'IN-tip' embodiment comprises additionally one or more heparin inhibitors, preferably heparinase, protamine, or protamine-related peptides, in dry, essentially dry or liquid formulation, or in any other formulation that allows for dissolution of the activator within 30 s after aspiration of the sample liquid. This embodiment is referred to as 'HEP-tip' in the following.

It is also preferred that the calcium salt in all embodiments mentioned above is selected from CaCl$_2$), Calcium-Lactate, Calcium-Gluconate, or any mixtures thereof in dry, essentially dry, or liquid formulation, or in any other formulation that allows for dissolution of the activator within 30 s after aspiration of the sample liquid.

If the diagnostic composition comprises more than two components to be separated in compartments (a) and (b), the additional components may also be placed in additional compartments (c), (d), etc. within the tip. Thus, the pipette tip may contain one or more compartments, for example 1, 2, 3, 4, or 5 compartments. Preferably, the more than two component(s) are combined, e.g. mixed, with constituent(s) (A) and/or (B), and, thus, compartments (a) and (b) are sufficient. However, it is also preferred that additional components, which are not comprised by constituent(s) (A) and/or (B) may be placed in additional compartments other than compartments (a) and (b).

If additional components of the diagnostic composition are mixed with either constituent (A) or (B), they must be in the same physical condition (i.e., liquid, dry, essentially dry, etc.). If they are placed in an additional compartment, they can have another physical condition. For example, one component in a first compartment is a dry formulation, while another component in a second compartment is a liquid formulation, and a third component is essentially dry formulation. In another example two components are mixed as liquids and one component may be dried in a separate compartment, or, in another example, two components are a dry mixture and one component may be a dried liquid in a separate compartment.

Preferred embodiments of a pipette tip containing constituents (A) and (B) in compartments (a) and (b), respectively, are shown in FIGS. 3a-3g. A first preferred embodiment, shown in FIG. 3a), is a pipette tip (11a), which has a conventional (merely conical) tip shape with open lower end (12a) and open upper end (13a) fitting to the pipette dimensions. Compartment (b) containing constituent (B) is represented by a porous insert (14a). Compartment (a) containing constituent (A) is represented by the lowest cross-wise section of the tip (below the porous insert (14a)) having an inner tip surface area of 1-1000 mm$^2$, on which a circumferential reagent layer (15a) of constituent (A) is deposited.

Another preferred embodiment, shown in FIG. 3b), is a pipette tip (11b) having a modified tip shape with open lower end (12b) and open upper end (13b) fitting to the pipette dimensions. Compartment (b) containing constituent (B) is represented by a porous insert (14b), wherein the porous insert (14b) has a cylindrical shape. Compartment (a) containing constituent (A) is represented by the lowest cross-wise section of the tip (below the porous insert (14a)) having an inner tip surface area of 1-1000 mm$^2$, on which a spot-like (not circumferential) reagent layer (15a) of constituent (A) is deposited.

Another preferred embodiment, shown in FIG. 3c), is a pipette tip (11c) having a modified tip shape with open lower end (12c) and open upper end (13c) fitting to the pipette dimensions. Pipette tip (11c) has two porous inserts (14c and 14c') forming compartment (a) comprising constituent (A) (14c) and compartment (b) comprising constituent (B) (14c'), the two porous inserts positioned adjacently to each other, wherein each of the porous inserts (14c, 14c') has a cylindrical shape with preferably the same diameter.

Another preferred embodiment, shown in FIG. 3d), is a pipette tip (11d), which has a conventional (merely conical) tip shape with open lower end (12d) and open upper end (13d) fitting to the pipette dimensions. Compartment (b) containing constituent (B) is represented by a porous insert (14d). Compartment (a) containing constituent (A) is represented by the cross-wise section of the tip just above the porous insert (14d) having an inner tip surface area of 1-1000 mm$^2$, on which a circumferential reagent layer (15d) of constituent (A) is deposited.

Another preferred embodiment, shown in FIG. 3e), is a pipette tip (11e), which has a conventional (merely conical) tip shape with open lower end (12e) and open upper end (13e) fitting to the pipette dimensions. Compartment (a) containing constituent (A) is represented by the lowest cross-wise section of the tip having an inner tip surface area of 1-1000 mm$^2$, on which a circumferential reagent layer (15e) of constituent (A) is deposited. Compartment (b) containing constituent (B) is represented by the cross-wise section of the tip just above compartment (a) having an inner tip surface area of 1-1000 mm$^2$, on which a circumferential reagent layer (15e') of constituent (B) is deposited.

Another preferred embodiment, shown in FIG. 3f), is a pipette tip (11f), which has a conventional (merely conical) tip shape with open lower end (12f) and open upper end (13f) fitting to the pipette dimensions. Compartment (a) containing constituent (A) is represented by the right longitudinal section of the tip, on which a spot-like (not circumferential) reagent layer (15f) of constituent (A) is deposited. Compartment (b) containing constituent (B) is represented by the left longitudinal section of the tip, on which a spot-like (not circumferential) reagent layer (15f) of constituent (B) is deposited.

In further preferred embodiments, an additional compartment (c) may be present, which may either be represented by an additional porous insert or by an additional tip section containing a reagent layer. Such a compartment (c) may be located in the pipette tip (i) above both, compartments (a) and (b); (ii) below both, compartments (a) and (b); or (iii) between compartment (a) and compartment (b).

Taken together, one of the several advantages of the pipette tip according to the present invention is that the constituent (A) contained in compartment (a) and the constituent (B) contained in compartment (b) can be optimized with regard to the long-term stability of the diagnostic composition. For example, if the TF has less stability when mixed with hexadimethrine bromide (polybrene), the TF can be placed in one compartment and the hexadimethrine bromide (polybrene) can be placed (optionally together with the calcium salt) in versa separated compartment. For example, if the TF has also less stability when mixed with Cytochalasin D, Cytochalasin D can also be placed in the compartment where the polybrene is placed. But, for example, if Cytochalasin D has less stability when mixed with hexadimethrine bromide (polybrene) in liquid phase, it can be eventually placed together with the TF in one compartment.

Thus, the pipette tip according to the present invention provides a considerable variety of options to increase reagent stability to the required level. This is achieved without the need for new automation technology for reagent filling or reagent handling and without adding new substances to the reagent composition.

Furthermore, it is preferable that the constituent (A) and/or the constituent (B) described herein additionally comprise a coagulation factor, preferably selected from FI, FII, FV, FVII, FVIII, FIX, FX, FXI, and FXIII or a coagulation inhibitor, preferably selected from TFPI, ATIII and APC.

Method and Use

In a second aspect the present invention provides a method of performing a diagnostic test on a sample, preferably a body fluid or blood sample, comprising the following steps:
(1) providing a pipette tip according to the present invention as described above;
(2) aspirating the sample into the pipette tip, thereby mixing, preferably dissolving, the constituent (A), e.g. contained in compartment (a), and the constituent (B), e.g. contained in compartment (b), of said pipette tip in the sample and obtaining a mixture, preferably a solution, of sample and constituents (A) and (B), wherein said mixture of constituent (A) and (B) form a diagnostic composition that is required to perform a diagnostic test;
(3) optionally, transferring the mixture of said sample and said diagnostic composition into a measurement container, such as a cuvette, suitable for performing said diagnostic test;
(4) optionally, putting the measurement container, such as the cuvette, into an apparatus suitable for performing said diagnostic test; and
(5) performing the diagnostic test of said mixture, optionally in the measurement container, such as a cuvette.

The sample is preferably a blood sample or a sample comprising a fraction of blood (e.g., isolated plasma or platelets), more preferably mammalian, in particular human blood or blood components or a fraction of blood. For example, the sample is whole blood or blood plasma, in particular human whole blood or human blood plasma. The sample may contain additional components added ex-vivo to the sample, for example acids, bases or buffers for modification, correction or stabilization of pH levels; and/or salts for modification, correction or stabilization of ion levels; and/or diluents to adjust the concentration of sample components to a required level like water, protein solutions, colloid solutions or and/or modifiers of the physical properties of the sample (e.g., oils or organic solvents to increase or decrease the sample viscosity; or surfactants to increase/decrease foam formation, etc.).

The diagnostic test performed in the method according to the present invention is preferably assessing the coagulation status of the sample and is, thus, a "coagulation test". Coagulation tests (also referred to as "blood clotting tests") are the tests used for diagnostics of the hemostasis system. Preferably, the coagulation test is a global coagulation test or a local coagulation test. Global tests characterize the results of work of the whole clotting cascade. They suit to diagnose the general state of the blood coagulation system and the intensity of pathologies, and to simultaneously record all attendant influences. Global methods play the key role at the first stage of diagnostics: they provide an integral picture of alterations within the coagulation system and allow predicting a tendency to hyper- or hypo-coagulation in general. Local tests characterize the results of work of the separate components of the blood coagulation system cascade, as well as of the separate coagulation factors. They are essential for the possibility to specify the pathology localization within the accuracy of coagulation factor. Preferred examples of a global coagulation tests include thromboelastography, thrombin generation test (thrombin potential, endogenous thrombin potential) and thrombodynamics test.

Preferred examples of a local coagulation tests include Partial thromboplastin time (PTT or APTT: activated partial thromboplastin time), Prothrombin time test (or prothrombin test, INR, PT) and other highly specialized methods to reveal the alteration in concentration of separate factors.

Preferably, the coagulation test measures:
(i) the time delay between coagulation activation and initial clotting (e.g., Prothrombin Time (PT), International Normalized Ratio (INR), Partial ThromboPlastin Time (PTT), activated Partial ThromboPlastin Time (aPTT), etc.); and/or
(ii) the platelet aggregation activity (e.g., by optical aggregometry or impedance aggregometry); and/or
(iii) the clot strength (e.g., by viscoelastic methods like thromboelastography or thromboelastometry); and/or
(iv) the clot lysis activity (e.g., by D-dimer level detection or clot strength decrease in viscoelastic methods).

In a coagulation test, the sample is preferably a blood sample or a fraction of a blood sample as described above.

Most preferably, the diagnostic test is a viscoelastic analysis.

Accordingly, it is preferred that the diagnostic test in step (5) comprises the determination of the clotting time, the clot formation time, the firmness of the clot over time, fibrinolysis activity (obtained as percentage of firmness reduction in relation to the maximum clot firmness), and/or any combination thereof.

The apparatus suitable for performing a diagnostic test, such as a viscoelastic analysis, is preferably a device as described in U.S. Pat. No. 5,777,215 A or in U.S. Pat. No. 6,537,819 B2. Another preferred example of an apparatus suitable for performing a viscoelastic analysis is schematically shown in FIG. 2. In more general, it is preferred that the apparatus suitable for performing a diagnostic test is a coagulometer. A coagulometer is a medical laboratory analyzer used for testing of the hemostasis system, in particular in coagulation tests. Modern coagulometers realize different methods of activation and observation of development of blood clots in blood or in blood plasma.

In more general, as used herein a viscoelastic analysis (also referred to as viscoelastic measurement) refers to a (viscoelastic) analysis of a sample, in particular a blood sample or a sample of blood elements, e.g. plasma or cells, in order to determine its coagulation characteristics, wherein such a viscoelastic analysis in the broadest sense is the measurement of a relative movement of a measurement container, such as a cuvette, containing a blood sample relative to a pin. In particular, in a typical viscoelastic analysis a clot is formed between measurement container and pin and thereafter the clot itself is stretched by the movement of the pin relative to the container. The detection of the characteristic parameters of the clot is based on the mechanical coupling of container and pin by the clot. In particular, a viscoelastic measurement provides information about several distinct parameters, for example the time between coagulation activation and clot initiation (clotting time CT), the dynamics of clot formation (clot formation time CFT), the firmness of the clot (amplitudes A5-A30 and maximum clot firmness MCF), and/or the extent of fibrinolysis (maximum lysis ML). Thus, the viscoelastic analysis preferably comprises the determination of the clotting time, the clot formation time, and/or the firmness of the clot over time including fibrinolytic effects. An exemplary diagram showing a typical viscoelastic analysis (also referred to as viscoelastic measurement) and the meaning of the parameters mentioned above is shown in FIG. 1. The clotting time CT is the initial lag time until the firmness starts to build up. The amplitude values A5-A30 are the firmness values 5-30 minutes after CT. The maximum lysis is the percentage decrease of firmness after the maximum value (MCF) was reached.

The positioning of the measurement container into an apparatus suitable for performing the diagnostic test (step (4)) is optional, since it may also occur at any time before. For example, all pipetting can also be performed while the measurement container is in the apparatus, if the apparatus provides enough access to the upper open end of the measurement container while placed in measurement position.

Preferably, the method of performing a diagnostic test, such as a viscoelastic analysis, on a sample according to the present invention further comprises a step (2-a) that follows step (2) and precedes step (3), wherein the tip is kept on the pipette for 1-30 s, preferably from 1-5 s. Thereby, a better or even complete reagent dissolution is allowed. Accordingly, in step (2-a) a short time delay of e.g. 1-30 s allows for complete dissolution of constituents (A) and (B) of the diagnostic composition within the sample. Additionally, the sample within the tip could be moved gently up and down within the pipette tip during step (2-a) by using the aspiration/dispensation functionality of the pipette, which is preferably realized in an automated sequence that does not require any user activity.

Preferably, each of steps (2) and (3) of the method of the present invention takes less than 30 sec, more preferably each of steps (2) and (3) takes from 2 to 10 s. Thereafter, the mixture of the sample and the diagnostic composition (optionally in the measurement container) is preferably quickly transferred to the measuring apparatus, more preferably in less than 30 s.

It is also preferred in the method according to the present invention that the method further comprises a step (3-a) following step (3) and preceding step (4), wherein in step (3-a) the mixture is at least partially re-aspired into the pipette tip and subsequently released again into the measurement container. This step may be repeated one or more, e.g. 2, 3, 4, 5, 6, 7, 8, 9, or 10 times. Thereby a better mixing of the sample is achieved and a better dissolution of constituents (A) and (B) is allowed.

No change of pipette tip is necessary when preparing one test. This shows the direct benefit of the present invention for the person who is performing such tests regarding the ease of use.

In a further aspect, the present invention also provides the use of a pipette tip as described above in a coagulation test as described above. Preferably, the pipette tip as described above is used in viscoelastic analysis as described above.

BRIEF DESCRIPTION OF THE FIGURES

In the following a brief description of the appended figures will be given. The figures are intended to illustrate the present invention in more detail. However, they are not intended to limit the subject matter of the invention in any way.

LIST OF REFERENCE SIGNS

Figure 1:
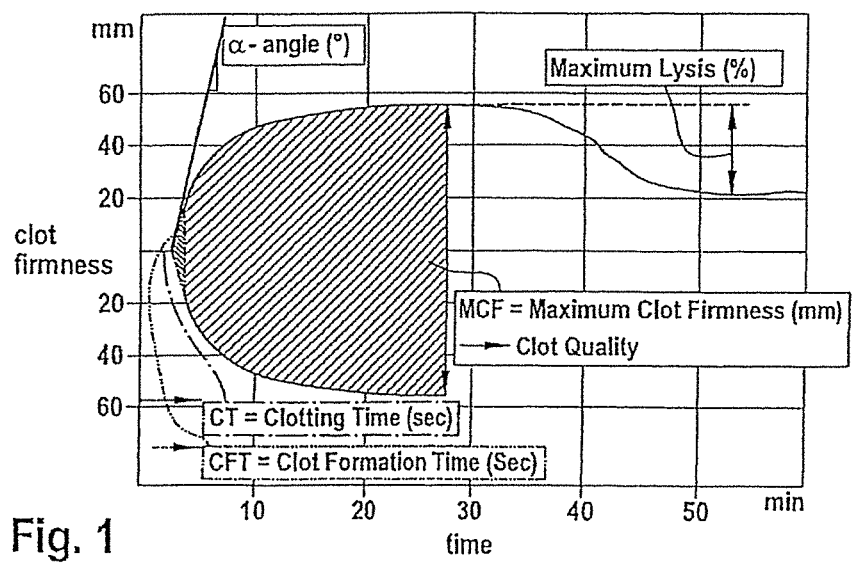
FIG. 1 is an exemplary diagram showing a typical viscoelastic measurement and corresponding curve parameters: clotting time CT is the lag time between activation of the sample and the time when a firmness value of 2 mm is reached; clot formation time CFT is the time that passes between the firmness values of 2 mm and 20 mm; alpha is the angle that is formed between the tangential of the firmness curve and the x-axis; maximum clot firmness MCF is the maximum firmness value of the curve; maximum lysis is the percentage decrease of firmness after MCF has been reached.
Figure 2:
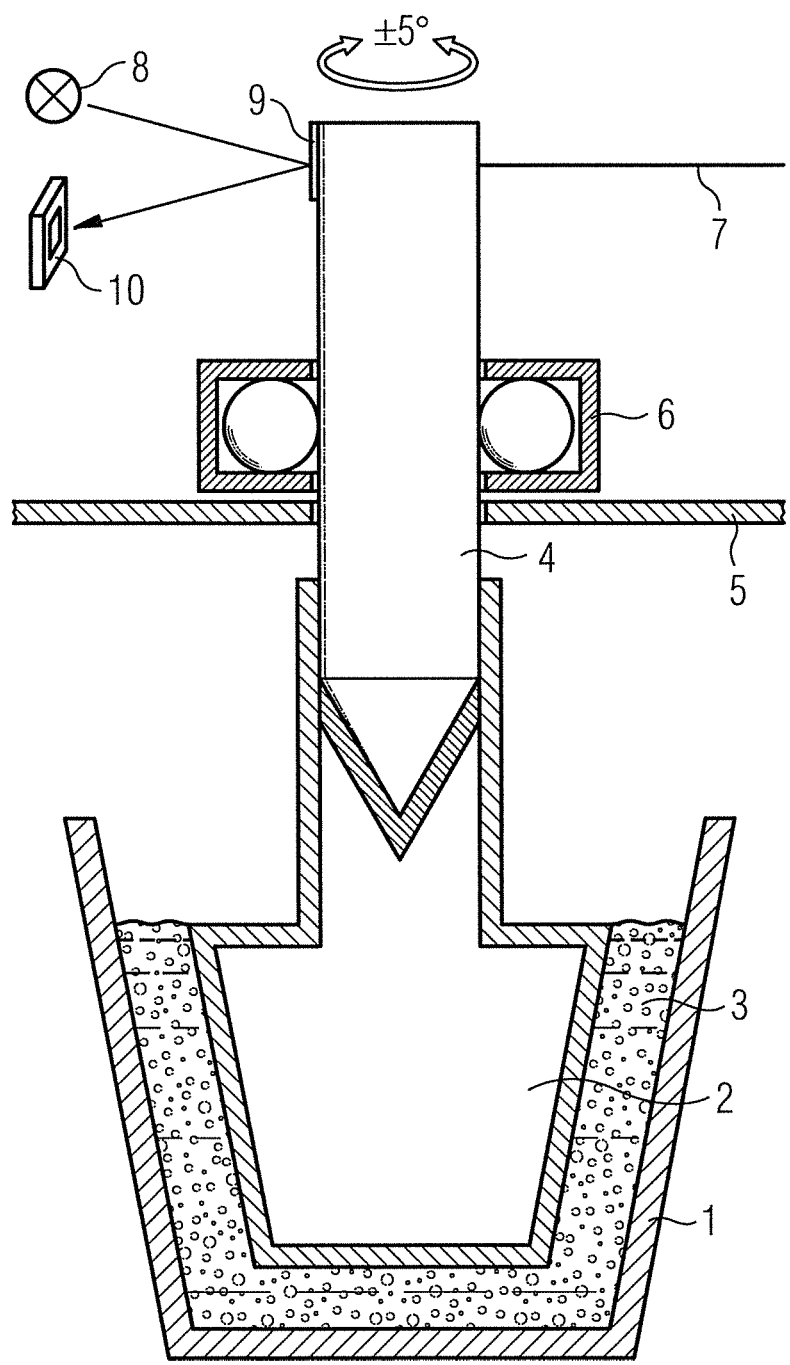
FIG. 2 shows an illustration of an apparatus for viscoelastic testing: After the formation of the clot between cup 1 (cuvette) and pin 2, the clot itself is stretched by the movement of the pin 2 relative to the cup 1. The detection of the characteristic parameters of the clot is based on the mechanical coupling of cup 1 and pin 2 by the clot. This is only possible if the clot adheres on the surfaces of both cup 1 and pin 2. Thus, a firm adhesion to the surfaces of both cup 1 and pin 2 is typically required for the viscoelastic analysis. During a viscoelastic measurement, the pin is fixed to the axis 4 and gently and slowly rotated in the cup via the spring 7. The axis 4 itself is fixed to the base plate 5 with the ball bearing 6. The movement of the pin is measured optically by illuminating the mirror 9 (fixed to the axis 4) with the light source 8 and detecting the reflected signal at the spatially resolving photo detector 10.
Figure 3A:
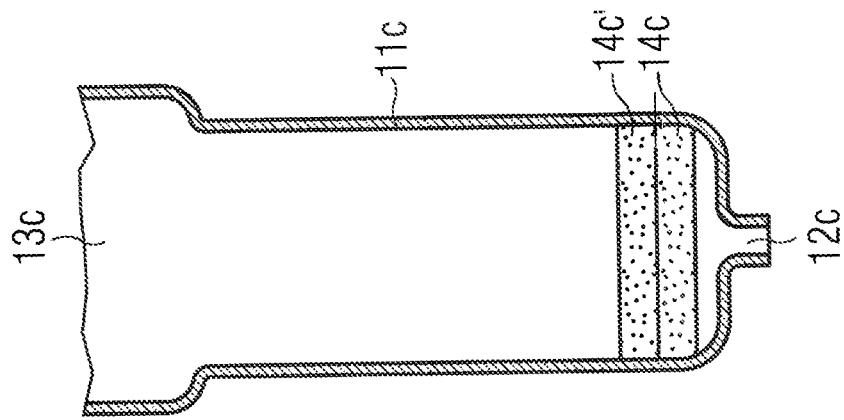
FIG. 3A shows a longitudinal cross-section through a conventional pipette tip (11a) containing constituents (A) and (B) with open lower end (12a), open upper end (13a) fitting to the pipette dimensions, porous insert (14a) and reagent layer (15a) below the porous insert (14a).
Figure 3B:
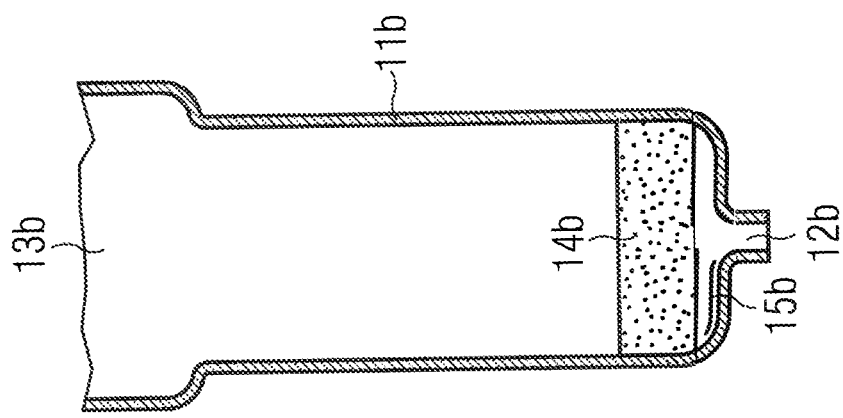
FIG. 3B shows a longitudinal cross-section through a modified pipette tip (11b) containing constituents (A) and (B) with open lower end (12b), open upper end (13b) fitting to the pipette dimensions, porous insert (14b) and reagent layer (15b) below the porous insert (14b).
Figure 3C:
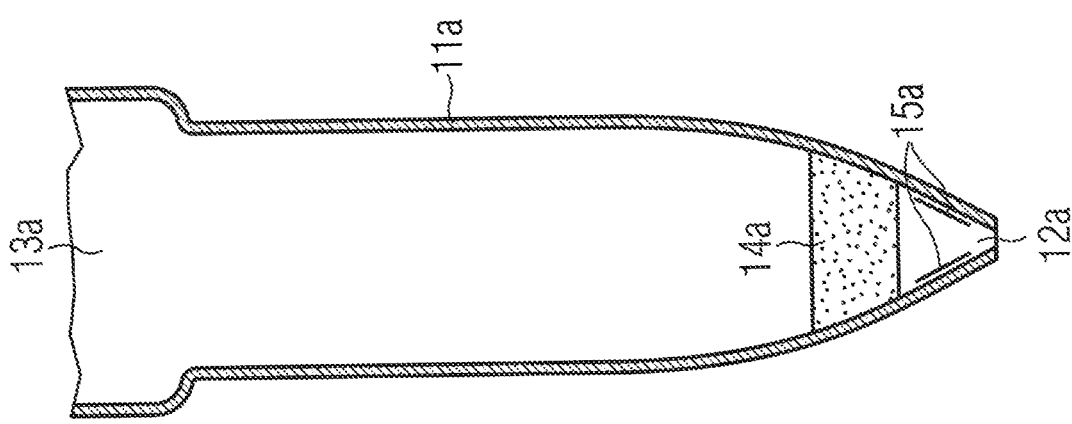
FIG. 3C shows a longitudinal cross-section through a modified pipette tip (11c) containing constituents (A) and (B) with open lower end (12c), open upper end (13c) fitting to the pipette dimensions, and two porous inserts (14c, 14c').
Figure 3D:
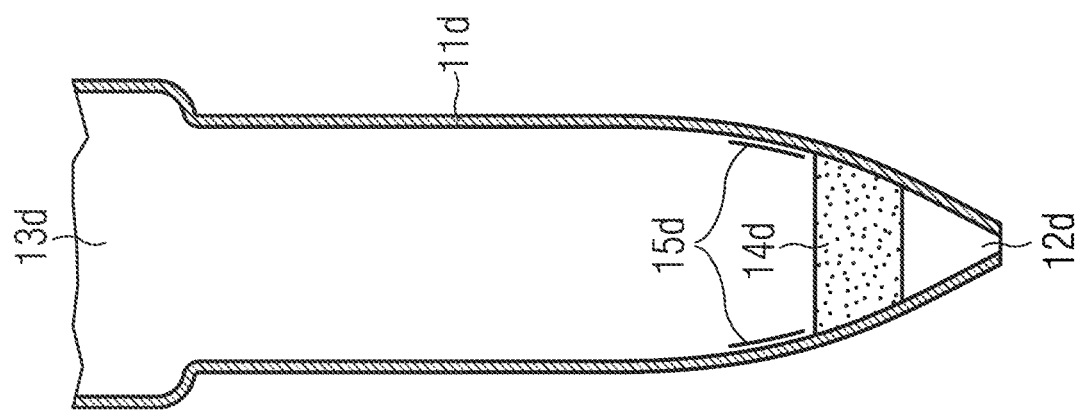
FIG. 3D shows a longitudinal cross-section through a conventional pipette tip (11d) containing constituents (A) and (B) with open lower end (12d), open upper end (13d) fitting to the pipette dimensions, porous insert (14d) and reagent layer (15d) above the porous insert (14d).
Figure 3E:
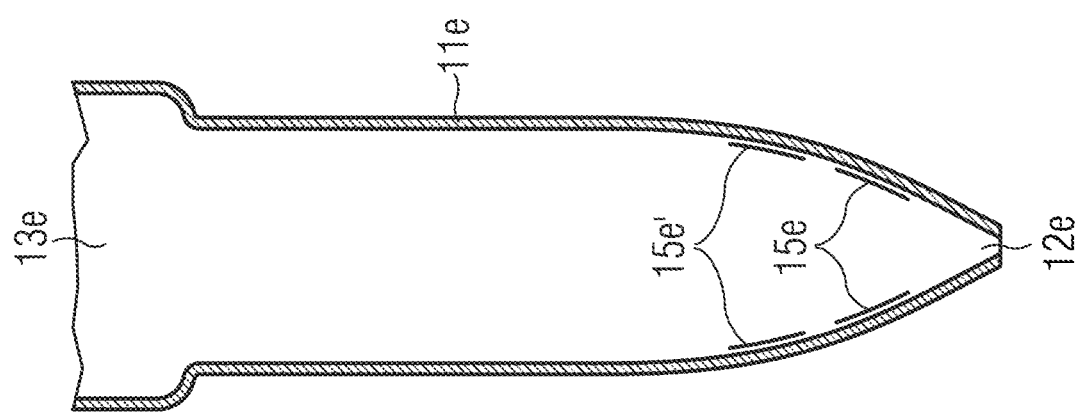
FIG. 3E shows a longitudinal cross-section through a conventional pipette tip (11e) containing constituents (A) and (B) with open lower end (12e), open upper end (13e) fitting to the pipette dimensions, and two circumferential reagent layers (15e, 15e') located on top of each other.
Figure 3F:
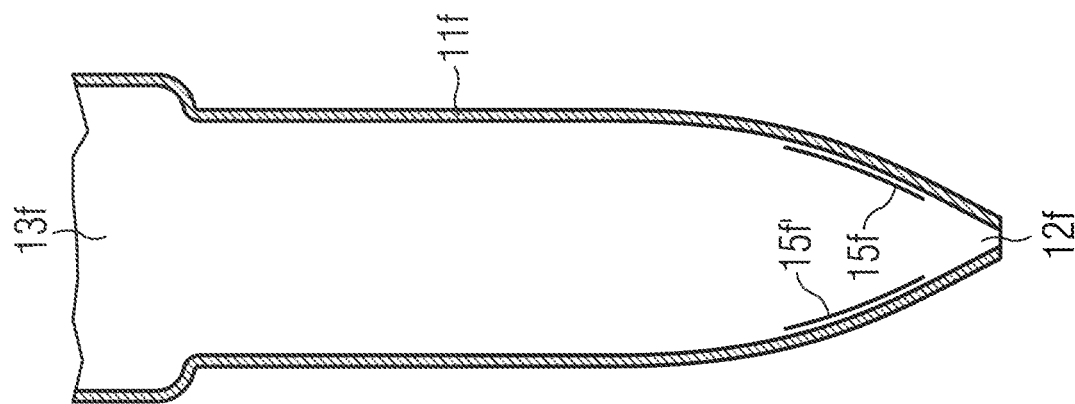
FIG. 3F shows a longitudinal cross-section through a conventional pipette tip (11f containing constituents (A) and (B) with open lower end (12f), open upper end (13f) fitting to the pipette dimensions, and two spot-like reagent layers (15f, 15f) located in juxtaposition.

| | |
|---|---|
| 1, 1a, 1b, 1c | measurement cup |
| 2, 2a, 2b, 2c | pin |
| 3 | sample |
| 4 | axis |
| 5 | base plate |
| 6 | ball bearing |
| 7 | spring |
| 8 | light source |
| 9 | mirror |
| 10 | detector |
| 11, 11a, 11b, 11c, 11d, 11e, 11f | pipette tip |

-continued

LIST OF REFERENCE SIGNS

| | |
|---|---|
| 12a, 12b, 12c, 12d, 12e, 12f | open lower end of the pipette tip |
| 13a, 13b, 13c, 13d, 13e, 13f | open upper end of the pipette tip |
| 14a, 14b, 14c, 14c', 14d | porous insert |
| 15a, 15b, 15d, 15e, 15e', 15f, 15f | reagent layer |

EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Effect of TF/Phospholipids Deposited Either in Compartment (a) or in Compartment (b) of the Pipette Tip on Clotting Time To investigate the effect of the extrinsic activator of coagulation on the clotting time when TF and phospholipids are deposited in dry form either in compartment (a) or in compartment (b), viscoelastic measurements of human plasma samples (10 donors mixed) were performed with a ROTEG® 05 device (Pentapharm GmbH, Munich, Germany). In the pipette tip used herein, compartment (b) was formed by a cylindrical porous insert made of polyether foam (RG 130 grey, Hildebrandt and Richter & Co. GmbH, Germany), the porous insert having a cylindrical shape of 5 mm height and 4 mm diameter. The porous insert was located in the lower half of the pipette tip. Compartment (a) of the pipette tip was provided by a crosswise section of the pipette tip, wherein a spot-like reagent layer of approximately 1.5 mm diameter (corresponding to about 4 µl liquid reagent before drying) was deposited.

Frozen plasma samples where freshly thawed and heated to 37° C. just before measurement. The source of TF/phospholipids was Innovin® (Siemens AG, Germany) and the source of $CaCl_2$) was Calcium Chloride Dihydrate (Sigma-Aldrich Chemie GmbH, Germany). Pipetting of TF was performed with Top-Line® 1 ml tips (AHN Biotechnologie GmbH, Germany) on a manual 1 ml pipettor (Brand, Germany). Liquid $CaCl_2$) was placed in the measurement cuvette just before TF pipetting was performed. The TF composition contained 15 ul of Innovin® standard stock solution together with 4% sucrose and was dried for 2 days in a desiccator filled with 100 g molecular sieve (4 Angstroem) after placing either in compartment (a) or in compartment (b). For the control experiment, the same sample was measured by using the standard liquid reagent provided for the ROTEG® 05 system (TEM Innovations GmbH, Germany).

Results are shown in Table 1 below.

TABLE 1

Clotting times (CT) obtained after placing the same amounts of TF in the pipette tip in either dry or wet form either in compartment (a) or in compartment (b). Each value was calculated as average of 4 measurements with human plasma. Mixed storage of TF and $CaCl_2$ impairs the clotting time CT severely (correction impossible), while mixing TF with 4% sucrose can compensate for degradation during storage and/or dissolution delays of pure TF.

| Activator | CT control | CT of dry TF in compartment (a) | CT of dry TF in compartment (b) | CT of wet TF in compartment (a) | CT of wet TF in compartment (b) |
|---|---|---|---|---|---|
| Tissue factor/ phospholipids | 57 sec | 61 sec | 239 sec | 55 sec | 168 sec |

Example 2: Effect of TF/Phospholipids Deposited in the Pipette Tip Alone or in Combination with $CaCl_2$ on Clotting Time To investigate the effect of the extrinsic activator of coagulation TF and phospholipids deposited in dry form in compartment (a) of the pipette tip either alone or in combination with $CaCl_2$ on the clotting time, viscoelastic measurements of human plasma samples (10 donors mixed) were performed with a ROTEG® 05 device (Pentapharm GmbH, Munich, Germany) according to the procedures described in Example 1. Compartment (a) of the pipette tip was provided by a crosswise section in the lower third of the pipette tip, wherein a spot-like reagent layer of about 2 mm diameter, corresponding to about 5 µl liquid reagent before drying, was deposited.

Results are shown in Table 2 below.

TABLE 2

Clotting times (CT) obtained after drying the same amounts of TF solution in compartment (a) of the pipette tip and storing for one week at room temperature. For the pure TF sample, the same amount of $CaCl_2$ as in the mixed sample was added just before the measurement (each value was calculated as average of 4 measurements with human plasma). Mixed storage of TF and $CaCl_2$ impairs the clotting time CT severely (correction impossible), while increasing the amount of TF by a factor of 4 and adding 2% sucrose can compensate for degradation of the pure TF sample during storage and/or dissolution delays.

| Activator | CT control | CT of TF/$CaCl_2$ mixture | CT of pure TF | CT of pure TF (4x concentr.) |
|---|---|---|---|---|
| Tissue factor/ phospholipids | 59 sec | >600 sec | 122 sec | 57 sec |

Taken together, the results of this experiment show that TF and $CaCl_2$ should not be stored mixed together. Thus, separation of TF and $CaCl_2$ into two spatially separated compartments (a) and (b) seems undoubtedly necessary.

Example 3: Effect of Ellagic Acid/Phospholipids Deposited in the Pipette Tip in Wet or Dry Form on Clotting Time To investigate the effect of an intrinsic activator of coagulation, namely ellagic acid and phospholipids, provided either in dry or in wet form in compartment (b) of the pipette tip (formed by a porous insert as described in Example 1) on clotting time, viscoelastic measurements were performed by using the equipment and procedures described in Example 1 above.

Results are shown in Table 3 below.

TABLE 3

Clotting times (CT) obtained by identical activator solutions without additives after storage as liquid or dried tip for 7 days at room temperature (tip insert made from polyether, each value was calculated as average of 4 measurements with human plasma). The wet storage of ellagic acid results in comparable CT values as the control, but the degradation during dry storage and/or dissolution delay can be compensated for by 35% more activator content and adding 2% sucrose.

| Activator | CT control | CT of dry tip | CT of wet tip | CT of dry tip (1.3x concentr.) |
|---|---|---|---|---|
| Ellagic acid/ phospholipids | 164 sec | 258 sec | 162 sec | 161 sec |

Example 4: Effect of $CaCl_2$ Deposited in the Pipette Tip in Either Wet or Dry Form in Compartment (a) or (b) on Clotting Time To investigate the effect of $CaCl_2$ deposited either in dry or in wet form in compartment (a) or (b) of the pipette tip, viscoelastic measurements were performed by using the procedures, equipment and compartment specifications as described in Example 1 above.

Results are shown in Table 4 below.

TABLE 4

Clotting times (CT) obtained after storing $CaCl_2$ in the tip for one week at room temperature (each value was calculated as average of 4 measurements with human plasma). No significant differences to the control CT are observed for all four approaches.

| Activator | CT control | $CaCl_2$ dry in compartment (a) | $CaCl_2$ wet in compartment (a) | $CaCl_2$ dry in compartment (b) | $CaCl_2$ wet in compartment (b) |
|---|---|---|---|---|---|
| Ellagic acid | 194 sec | 207 sec | 205 sec | 192 sec | 189 sec |

What is claimed is:

1. A pipette tip comprising a constituent (A) and a constituent (B), the pipette tip having:
   an open upper end configured to fit to an end of a pipette;
   an open lower end configured to aspirate and release a liquid sample;
   a longitudinal axis spanning a length from the open upper end to the open lower end;
   an inner surface;
   a first reagent layer deposited on a first region of the inner surface; and
   a second reagent layer deposited on a second region of the inner surface;
   wherein the first reagent layer comprises constituent (A) and the second reagent layer a comprises constituent (B),
   constituent (A) being physically confined and releasably coupled to the first region and being separate from constituent (B), and
   constituent (B) being physically confined and releasably coupled to the second region and being separate from constituent (A),
   wherein:
   (a) the first region and the second region are non-overlapping,
   (b) constituent (A) is different than constituent (B);
   (c) constituent (A) and constituent (B) are configured to form a diagnostic composition upon their release into the liquid sample from the first region and the second region; and
   (d) wherein each of the constituents (A) and (B) is an essentially dry formulation or a dry formulation deposited on the inner surface;
   (e) the first region and the second region are juxtaposed opposite the longitudinal axis from each other.

2. The pipette tip according to claim 1, wherein at least one of constituents (A) and (B) comprises an activator of coagulation.

3. The pipette tip according to claim 2, wherein the activator of coagulation is an extrinsic activator.

4. The pipette tip according to claim 2, wherein the activator of coagulation is an intrinsic activator of coagulation.

5. The pipette tip according to claim 3, wherein the extrinsic activator is a Tissue Factor (TF).

6. The pipette tip according to claim 4, wherein the intrinsic activator of coagulation is selected from the group consisting of celite, ellagic acid, sulfate, kaolin, silica, RNA, and mixtures thereof.

7. The pipette tip according to claim 1, wherein at least one of constituents (A) and (B) comprises a coagulation activating factor.

8. The pipette tip according to claim 1, wherein at least one of constituents (A) and (B) comprises an active-component inhibitor that is selected from one or more platelet inhibitors, fibrinolysis inhibitors, and/or heparin inhibitors.

9. The pipette tip according to claim 1, wherein at least one of constituents (A) and (B) comprises a cytoskeleton inhibitor and/or a GPIIb/IIIa antagonist.

10. The pipette tip according to claim 7, wherein the coagulation activating factor is selected from the group consisting of FI, FII, FV, FVII, FVIII, FIX, FX, FXI, FXIII, and TF.

11. The pipette tip according to claim 10, wherein the coagulation inhibitor is selected from tissue factor pathway inhibitor, antithrombin I-IV, or activated protein C.

12. The pipette tip according to claim 5, wherein the Tissue Factor (TF) is selected from the group consisting of lipidated TF, rIF, and combinations thereof.

13. The pipette tip according to claim 8, wherein the active-component inhibitor is hexadimethrine bromide (polybrene).

14. The pipette tip according to claim 1, wherein at least one of constituents (A) and (B) comprises a calcium salt.

15. The pipette tip according to claim 1, wherein at least one of constituents (A) and (B) comprises a fibrinolysis inhibitor selected from the group consisting of aprotinin, tranexamic acid, eaca, thrombin-activated fibrinolysis inhibitor, plasminogen activation inhibitor 1/2, α2-antiplasmin, and α2-macroglobulin.

16. The pipette tip according to claim 1, wherein at least one of constituents (A) and (B) comprises a heparin inhibitor selected from the group consisting of heparinase, protamine, protamine-related peptides and their derivatives, and cationic polymers.

17. The pipette tip according to claim 1, wherein at least one of constituents (A) and (B) comprises a coagulation inhibitor.

* * * * *